United States Patent
Boral et al.

(10) Patent No.: US 9,353,093 B2
(45) Date of Patent: May 31, 2016

(54) INDOLE-1-CARBOXAMIDES AS KINASE INHIBITORS

(71) Applicant: Allergan, Inc., Irvine, CA (US)

(72) Inventors: Sougato Boral, Irvine, CA (US);
Thomas C. Malone, Irvine, CA (US);
Shimiao Wang, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/509,007

(22) Filed: Oct. 7, 2014

(65) Prior Publication Data
US 2016/0096828 A1 Apr. 7, 2016

(51) Int. Cl.
*C07D 209/04* (2006.01)
*C07D 409/14* (2006.01)
*C07D 209/26* (2006.01)
*C07D 405/12* (2006.01)
*C07D 409/04* (2006.01)

(52) U.S. Cl.
CPC ............ *C07D 409/14* (2013.01); *C07D 209/26* (2013.01); *C07D 405/12* (2013.01); *C07D 409/04* (2013.01)

(58) Field of Classification Search
CPC .................................................. C07D 209/04
See application file for complete search history.

(56) References Cited

U.S. PATENT DOCUMENTS

| | | | |
|---|---|---|---|
| 3,360,200 A | 12/1967 | Purtell | |
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,366,738 A | 11/1994 | Rork et al. | |
| 7,169,780 B2 | 1/2007 | Crescenzi et al. | |
| 7,265,125 B2 | 9/2007 | Breu et al. | |
| 8,221,737 B2 | 7/2012 | Or et al. | |
| 2009/0093472 A1 | 4/2009 | Paradkar et al. | |
| 2009/0163545 A1 | 6/2009 | Goldfarb | |
| 2010/0316607 A1 | 12/2010 | Or et al. | |
| 2011/0008288 A1 | 1/2011 | Or et al. | |
| 2012/0178752 A1 | 7/2012 | Ginn et al. | |

FOREIGN PATENT DOCUMENTS

| WO | 99-62890 A1 | 12/1999 |
|---|---|---|
| WO | 2005-082001 A2 | 9/2005 |
| WO | 2006-026034 A2 | 3/2006 |
| WO | 2007-091106 A2 | 8/2007 |
| WO | 2009-019504 A1 | 2/2009 |
| WO | WO 2009/019504 A1 * | 2/2009 |
| WO | 2009-075874 A1 | 6/2009 |
| WO | 2010148006 A1 | 12/2010 |

OTHER PUBLICATIONS

Nobuo Jo, Carolina Mailhos, et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, Jun. 2006.
Justine R Smith, et al., Expression of vascular endothelial growth factor and its receptors in rosacea, Br J Ophthalmol 2007;91:226-229. doi: 10.1136/bjo.2006.101121.
S. W. Cowan-Jacob, et al., Structural biology of protein tyrosine kinases, Cell. Mol. Life Sci. 63 (2006) 2608-2625.
Regina Heidenreich, et al., Angiogenesis: The New Potential Target for the Therapy of Psoriasis?Drug News Perspect 21(2), Mar. 2008.
Aimee V. Chappelow et al., Neovascular Age-Related Macular Degeneration, Potential Therapies, Drugs 2008; 68(8): 1029-1036.
Mark Rami Barakat, et al., VEGF inhibitors for the treatment of neovascular age-related macular degeneration, Expert Opin. Investig. Drugs (2009) 18(5).
Xinyuan Zhang, et al., Vascular endothelial growth factor-A: A multifunctional molecular player in diabetic retinopathy, The International Journal of Biochemistry & Cell Biology 41 (2009) 2368-2371.
Zhang Ni, et al., Emerging Pharmacologic Therapies for Wet Age-Related Macular Degeneration, Ophthalmologica 2009;223:401-410.
Jayne M. Stommel et al., Coactivation of Receptor Tyrosine Kinases Affects the Response of Tumor Cells to Targeted Therapies, www.sciencemag.org, Science vol. 318 Oct. 12, 2007.
Arora, A. et al., Role of Tyrosine Kinase Inhibitors in Cancer Therapy, The Journal of Pharmacology & Experimental Therapeutics, 2005, 315: 971-979 (3).
Bergers, G. et al., Benefits of targeting both pericytes and endothelial cells in the tumor vasculature with kinase inhibitors, The Journal of Clinical Investigation 2003, 111: 1287-1295 (9).
Cross, L.C. et al., Rules for the Nomenclature of Organic Chemistry Section E: Stereochemistry, Pure & Applied Chemistry 1976, 45: 11-30.
Stahl, P.H. et al., Handbook of Pharmaceutical Salts, Properties, Selection, and and Use, 2002, 330-345.
Remington's Pharmaceutical Sciences, 1980, pp. 1-10.

* cited by examiner

*Primary Examiner* — Shawquia Jackson
(74) *Attorney, Agent, or Firm* — Jonathan Bass

(57) ABSTRACT

This invention is directed to a compound of Formula I

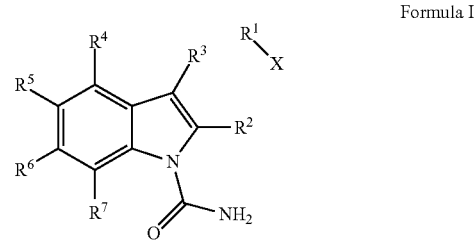

Formula I or a pharmaceutically acceptable salt thereof, wherein $R^1$, $R^2$, $R^3$, $R^4$, $R^5$, $R^6$, $R^7$, and X are as defined herein. The compounds of Formula I are useful as receptor tyrosine kinase (RTK) inhibitors and can be used to treat such diseases as cancer, blood vessel proliferative disorders, fibrotic disorders, mesangial cell proliferative disorders and metabolic diseases.

14 Claims, No Drawings

INDOLE-1-CARBOXAMIDES AS KINASE INHIBITORS

FIELD OF THE INVENTION

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

DESCRIPTION OF THE RELATED ART

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phophorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2996, 63, 2608-2625.

There are a number of examples where RTK kinases, have been found to be involved in cellular signaling pathways leading to pathological conditions, including wet age-related macular degeneration (Ni et al. Opthalmologica 2009 223 401-410; Chappelow et al. Drugs 2008 68 1029-1036), diabetic retinopathy (Zhang et al Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105) and hyper immune response. In ophthalmic diseases such as neovascular age-related macular degeneration and diabetic retinopathy aberrant activation of VEGF receptors can lead to abnormal blood vessel growth. The importance of VEGFR signaling in the neovascular age-related macular degeneration disease process is evident by the clinical success of multiple anti-VEGF targeting agents including Lucentis®, Avastin®, and EYLEA™ (Barakat et al. Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as neovascular age-related macular degeneration and diabetic retinopathy the inhibition of both VEGFR and PDGFRβ may provide a greater therapeutic effect in by causing regression of existing neovascular blood vessels present in the disease (Adamis et al. Am. J. Pathol. 2006 168 2036-2053). In cancer inhibition of multiple RTK signaling pathways has been suggested to have a greater effect than inhibiting a single RTK pathway (DePinho et al. Science 2007 318 287-290; Bergers et al. J. Clin Invest. 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Certain small compounds are disclosed in PCT publication No. WO/1999/062890, PCT publication No. WO/2005/082001 and PCT publication No. WO/2006/026034 as useful for the treatment of diseases related to unregulated TKS transduction. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

US2009/0163545 refers to methods of using lifespan-altering compounds for altering the lifespan of eukaryotic organisms and screening for such compounds.

WO2009/019504 refers to the preparation of benzoxazoles, benzimidazoles, indoles and their analogs for the treatment of muscular dystrophy and cachexia.

WO2007/091106 refers to the preparation of benzoxazoles, benzimidazoles, indoles and their analogs for the treatment of muscular dystrophy and cachexia.

KR 2011033395 refers to the preparation of benzoxazolyl-pyridine derivatives as protein kinase inhibitors.

WO2009/075874 refers to the preparation of N-[4-pyridin-4-yl)phenyl]amides as gamma-secretase modulators.

SUMMARY OF THE INVENTION

The present invention relates to organic molecules capable of modulating, regulating and/or inhibiting protein kinase RNA-activated (protein kinase R; PKR) and tyrosine kinase signal transduction. Such compounds are useful for the treatment of diseases related to unregulated TKS transduction, including cell proliferative diseases such as cancer; vascular (blood vessel) proliferative disorders such as diabetic retinopathy, age-related macular degeneration, retinopathy of prematurity, pterigium, arthritis and restenosis; fibrotic disorders such as hepatic cirrhosis and atherosclerosis; mesangial cell proliferative disorder such as glomerulonephritis, diabetic nephropathy, malignant nephrosclerosis, thrombotic microangiopathy syndromes, transplant rejection and glomerulopathies; metabolic disorders such as psoriasis, diabetes mellitus, wound healing, inflammation and neurodegenerative diseases.

In one aspect, the invention provides a compound represented by Formula I or a pharmaceutically acceptable salt thereof or stereoisomeric forms thereof, or the enantiomers, diastereoisomers, tautomers, zwitterions and pharmaceutically acceptable salts thereof:

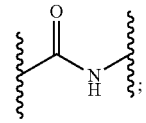

Formula I wherein:
$R^1$ is substituted or unsubstituted heterocycle or substituted or unsubstituted aryl;

X is 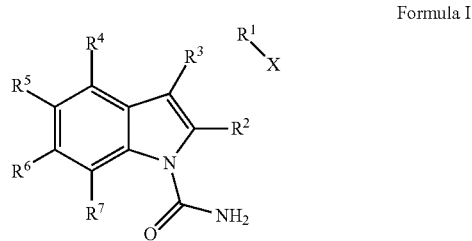 or

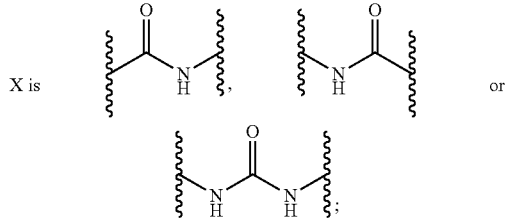

$R^2$ is substituted or unsubstituted heterocycle or substituted or unsubstituted aryl;

$R^3$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^4$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^5$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^6$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^7$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^8$ is substituted or unsubstituted $C_{1-8}$ alkyl, hydrogen, fluoro, —$CH_2OH$, —OH, $COCH_3$, $CH_2CH_2OH$, $CH_2CH_2CH_2OH$ or $CH_2CH_2OCH_2CH_2OH$;

$R^9$ is substituted or unsubstituted $C_{1-8}$ alkyl, hydrogen, fluoro or —OH;

$R^{10}$ is substituted or unsubstituted $C_{1-8}$ alkyl or hydrogen;

$R^{11}$ is substituted or unsubstituted $C_{1-8}$ alkyl, hydrogen or can form together with the N and $R^{12}$ a substituted or unsubstituted heterocycle;

$R^{12}$ is substituted or unsubstituted $C_{1-8}$ alkyl, hydrogen or can form together with the N and $R^{11}$ a substituted or unsubstituted heterocycle; and a is 0, 1, 2, 3 or 4.

In another aspect, the invention provides a compound represented by Formula I wherein:
$R^1$ is substituted or unsubstituted heterocycle or substituted or unsubstituted aryl;

X is

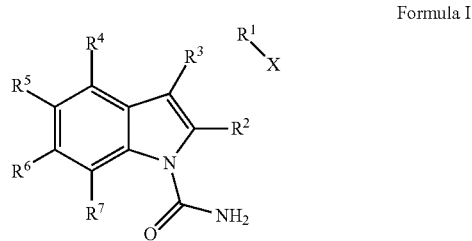

$R^2$ is substituted or unsubstituted heterocycle or substituted or unsubstituted aryl;

$R^3$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^4$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^5$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^6$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^7$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^8$ is substituted or unsubstituted $C_{1-8}$ alkyl, hydrogen, fluoro, —$CH_2OH$, —OH, $COCH_3$, $CH_2CH_2OH$, $CH_2CH_2CH_2OH$ or $CH_2CH_2OCH_2CH_2CH_2H$;

$R^9$ is substituted or unsubstituted $C_{1-8}$ alkyl, hydrogen, fluoro or —OH;

$R^{10}$ is substituted or unsubstituted $C_{1-8}$ alkyl or hydrogen;

$R^{11}$ is substituted or unsubstituted $C_{1-8}$ alkyl, hydrogen or can form together with the N and $R^{12}$ a substituted or unsubstituted heterocycle;

$R^{12}$ is substituted or unsubstituted $C_{1-8}$ alkyl, hydrogen or can form together with the N and $R^{11}$ a substituted or unsubstituted heterocycle; and a is 0, 1, 2, 3 or 4.

In another aspect, the invention provides a compound represented by Formula I wherein:

$R^1$ is substituted or unsubstituted heterocycle or substituted or unsubstituted aryl;

X is $R^2$ is substituted or unsubstituted heterocycle or substituted or unsubstituted aryl;

$R^3$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^4$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^5$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^6$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^7$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^8$ is substituted or unsubstituted $C_{1-8}$ alkyl, hydrogen, fluoro, —$CH_2OH$, —OH, $COCH_3$, $CH_2CH_2OH$, $CH_2CH_2CH_2OH$ or $CH_2CH_2OCH_2CH_2CH_2H$;

$R^9$ is substituted or unsubstituted $C_{1-8}$ alkyl, hydrogen, fluoro or —OH;

$R^{10}$ is substituted or unsubstituted $C_{1-8}$ alkyl or hydrogen;

$R^{11}$ is substituted or unsubstituted $C_{1-8}$ alkyl, hydrogen or can form together with the N and $R^{12}$ a substituted or unsubstituted heterocycle;

$R^{12}$ is substituted or unsubstituted $C_{1-8}$ alkyl, hydrogen or can form together with the N and $R^{11}$ a substituted or unsubstituted heterocycle; and a is 0, 1, 2, 3 or 4.

In another aspect, the invention provides a compound represented by Formula I wherein:

$R^1$ is substituted or unsubstituted heterocycle or substituted or unsubstituted aryl;

X is $R^2$ is substituted or unsubstituted heterocycle or substituted or unsubstituted aryl;

$R^3$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^4$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^5$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^6$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^7$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^8$ is substituted or unsubstituted $C_{1-8}$ alkyl, hydrogen, fluoro, —$CH_2OH$, —OH, $COCH_3$, $CH_2CH_2OH$, $CH_2CH_2CH_2OH$ or $CH_2CH_2OCH_2CH_2OH$;

$R^9$ is substituted or unsubstituted $C_{1-8}$ alkyl, hydrogen, fluoro or —OH;

$R^{10}$ is substituted or unsubstituted $C_{1-8}$ alkyl or hydrogen;

$R^{11}$ is substituted or unsubstituted $C_{1-8}$ alkyl, hydrogen or can form together with the N and $R^{12}$ a substituted or unsubstituted heterocycle;

$R^{12}$ is substituted or unsubstituted $C_{1-8}$ alkyl, hydrogen or can form together with the N and $R^{11}$ a substituted or unsubstituted heterocycle; and a is 0, 1, 2, 3 or 4.

In another aspect, the invention provides a compound represented by Formula I wherein:
$R^1$ is substituted or unsubstituted heterocycle;
X is

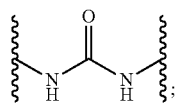

$R^2$ is substituted or unsubstituted aryl;
$R^3$ is hydrogen, substituted or unsubstituted $C_1$-$C_8$ alkyl, halogen;
$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

In another aspect, the invention provides a compound represented by Formula I wherein:
$R^1$ is substituted or unsubstituted aryl;
X is

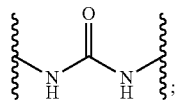

$R^2$ is substituted or unsubstituted heterocycle;
$R^3$ is hydrogen, substituted or unsubstituted $C_1$-$C_8$ alkyl, halogen;
$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

In another aspect, the invention provides a compound represented by Formula I wherein:
$R^1$ is substituted or unsubstituted aryl;
X is

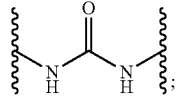

$R^2$ is substituted or unsubstituted aryl;
$R^3$ is hydrogen, substituted or unsubstituted $C_1$-$C_8$ alkyl, halogen;

$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

In another aspect, the invention provides a compound represented by Formula I wherein:
$R^1$ is substituted or unsubstituted heterocycle;
X is

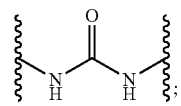

$R^2$ is substituted or unsubstituted heterocyle;
$R^3$ is hydrogen, substituted or unsubstituted $C_1$-$C_8$ alkyl, halogen;
$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

In another aspect, the invention provides a compound represented by Formula I wherein:
$R^1$ is substituted or unsubstituted heterocycle;
X is

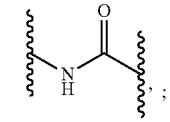 [SMILES: *NC(*)=O]

$R^2$ is substituted or unsubstituted aryl;
$R^3$ is hydrogen, substituted or unsubstituted $C_1$-$C_8$ alkyl, halogen;
$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

In another aspect, the invention provides a compound represented by Formula I wherein:
$R^1$ is substituted or unsubstituted aryl;
X is

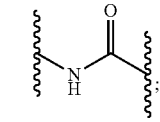 [SMILES: *NC(*)=O]

$R^2$ is substituted or unsubstituted heterocycle;
$R^3$ is hydrogen, substituted or unsubstituted $C_1$-$C_8$ alkyl, halogen;

$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

In another aspect, the invention provides a compound represented by Formula I wherein:
$R^1$ is substituted or unsubstituted aryl;
X is H;

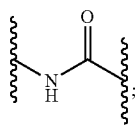 [SMILES: *NC(*)=O]

$R^2$ is substituted or unsubstituted aryl;
$R^3$ is hydrogen, substituted or unsubstituted $C_1$-$C_8$ alkyl, halogen;
$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

In another aspect, the invention provides a compound represented by Formula I wherein:
$R^1$ is substituted or unsubstituted heterocycle;
X is

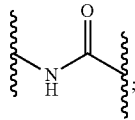

$R^2$ is substituted or unsubstituted heterocyle;
$R^3$ is hydrogen, substituted or unsubstituted $C_1$-$C_8$ alkyl, halogen;
$R^4$ is hydrogen, substituted or unsubstituted $C_1$-$C_8$ alkyl, halogen;
$R^5$ is hydrogen, substituted or unsubstituted $C_1$-$C_8$ alkyl, halogen;
$R^6$ is hydrogen, substituted or unsubstituted $C_1$-$C_8$ alkyl, halogen; and
$R^7$ is hydrogen, substituted or unsubstituted $C_1$-$C_8$ alkyl, halogen.

The term "alkyl", as used herein, refers to saturated, monovalent or divalent hydrocarbon moieties having linear or branched moieties or combinations thereof and containing 1 to 8 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$C_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon moiety having 2 to 6 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon moiety having 2 to 6 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, —OC$_{1-6}$ alkyl groups, —SC$_{1-6}$ alkyl groups, —C$_{1-6}$ alkyl groups, —C$_{2-6}$ alkenyl groups, —C$_{2-6}$ alkynyl groups, ketone groups, aldehydes, alkylamino groups, amino groups, aryl groups, C$_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)R$^x$ wherein R$^x$ can be alkyl, aryl, cycloalkyl, cycloalkenyl, heterocycle as defined above.

The term "ester" as used herein, represents an organic compound having a carbonyl group linked to a carbon atom such as —C(O)OR$^x$ wherein R$^x$ can be alkyl, aryl, cycloalkyl, cycloalkenyl, heterocycle as defined above.

The term "amine" as used herein, represents a group of formula "—NR$^x$R$^y$", wherein R$^x$ and R$^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$," or "NR$^x$R$^y$C(O)—," wherein R$^x$ and R$^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Other defined terms are used throughout this specification:
"Ac" refers to acetyl
"Et" refers to ethyl
"iPr" refers to i-propyl
"Me" refers to methyl
"MeOH" refers to methanol
"PDGF" refers to platelet derived growth factor
"Ph" refers to phenyl
"PTKs" refers to protein tyrosine kinase
"RTKs" refers to receptor tyrosine kinase
"rt" refers to room temperature
"tBu" refers to t-butyl.
"THF" refers to tetrahydrofuran
"VEGF" refers to vascular endothelial growth factor
"VEGFR" refers to vascular endothelial growth factor receptor Compounds of the invention are tabulated in Table 1:

TABLE 1

List of compound names and structures

| Example | Structure | Compound Name |
|---|---|---|
| 1 | 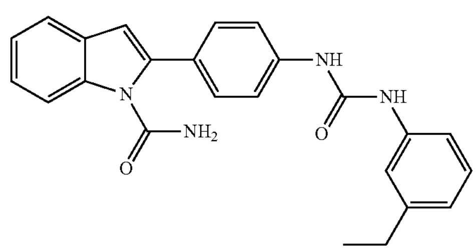 [SMILES: CCc1cccc(NC(=O)Nc2ccc(-c3cc4ccccc4n3C(N)=O)cc2)c1] | 2-[4-({[(3-ethylphenyl)amino]carbonyl}amino)phenyl]-1H-indole-1-carboxamide |
| 2 | 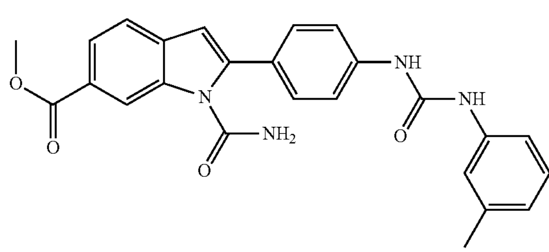 [SMILES: COC(=O)c1ccc2cc(-c3ccc(NC(=O)Nc4cccc(C)c4)cc3)n(C(N)=O)c2c1] | methyl 1-(aminocarbonyl)-2-[4-({[(3-methylphenyl)amino]carbonyl}amino)phenyl]-1H-indole-6-carboxylate |

TABLE 1-continued

List of compound names and structures

| Example | Structure | Compound Name |
|---------|-----------|---------------|
| 3 | 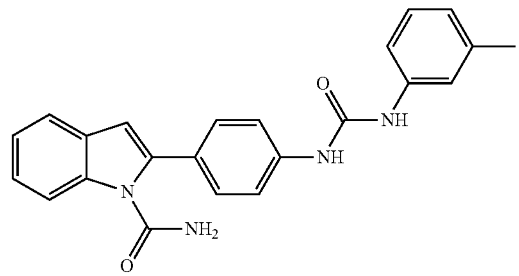 [SMILES: Cc1cccc(NC(=O)Nc2ccc(-c3cc4ccccc4n3C(N)=O)cc2)c1] | 2-[4-({[(3-methylphenyl)amino]carbonyl}amino)phenyl]-1H-indole-1-carboxamide |
| 4 | 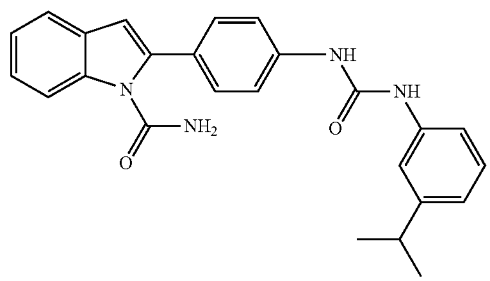 [SMILES: CC(C)c1cccc(NC(=O)Nc2ccc(-c3cc4ccccc4n3C(N)=O)cc2)c1] | 2-[4-({[(3-isopropylphenyl)amino]carbonyl}amino)phenyl]-1H-indole-1-carboxamide |
| 5 | 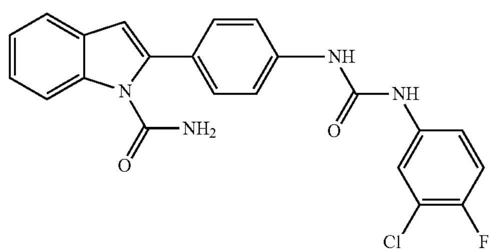 [SMILES: NC(=O)n1c(-c2ccc(NC(=O)Nc3ccc(F)c(Cl)c3)cc2)cc2ccccc21] | 2-[4-({[(3-chloro-4-fluorophenyl)amino]carbonyl}amino)phenyl]-1H-indole-1-carboxamide |
| 6 | 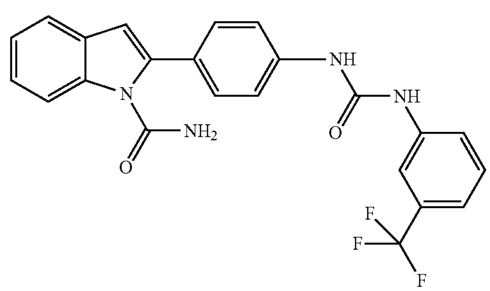 [SMILES: NC(=O)n1c(-c2ccc(NC(=O)Nc3cccc(C(F)(F)F)c3)cc2)cc2ccccc21] | 2-{4-[({[3-(trifluoromethyl)phenyl]amino}carbonyl)amino]phenyl}-1H-indole-1-carboxamide |
| 7 | 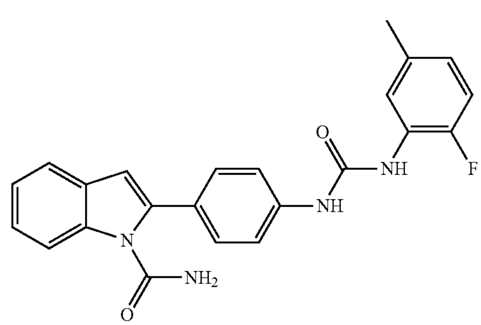 [SMILES: Cc1ccc(F)c(NC(=O)Nc2ccc(-c3cc4ccccc4n3C(N)=O)cc2)c1] | 2-[4-({[(2-fluoro-5-methylphenyl)amino]carbonyl}amino)phenyl]-1H-indole-1-carboxamide |

TABLE 1-continued

List of compound names and structures

| Example | Structure | Compound Name |
|---|---|---|
| 8 | 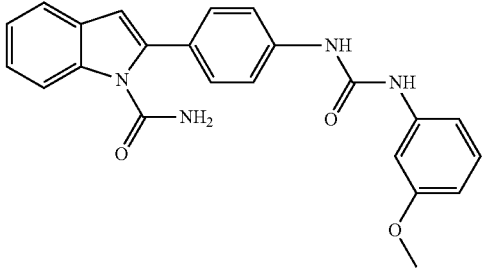 [SMILES: COc1cccc(NC(=O)Nc2ccc(-c3cc4ccccc4n3C(N)=O)cc2)c1] | 2-[4-({[(3-methoxyphenyl)amino]carbonyl]amino)phenyl]-1H-indole-1-carboxamide |
| 9 | 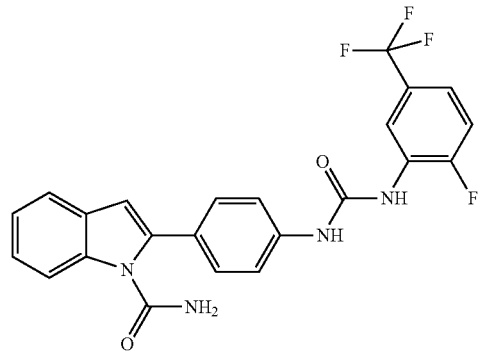 [SMILES: NC(=O)n1c(-c2ccc(NC(=O)Nc3cc(C(F)(F)F)ccc3F)cc2)cc2ccccc21] | 2-{4-[({[2-fluoro-5-(trifluoromethyl)phenyl]amino}carbonyl)amino]phenyl}-1H-indole-1-carboxamide |
| 10 | 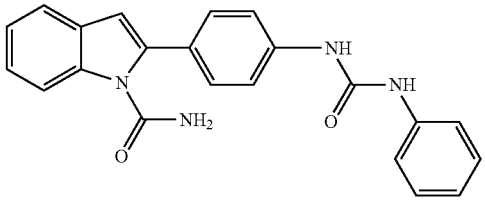 [SMILES: NC(=O)n1c(-c2ccc(NC(=O)Nc3ccccc3)cc2)cc2ccccc21] | 2-{4-[(anilinocarbonyl)amino]phenyl}-1H-indole-1-carboxamide |
| 11 | 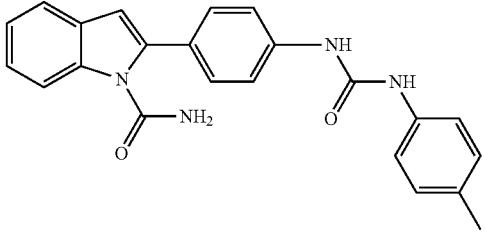 [SMILES: Cc1ccc(NC(=O)Nc2ccc(-c3cc4ccccc4n3C(N)=O)cc2)cc1] | 2-[4-({[(4-methylphenyl)amino]carbonyl}amino)phenyl]-1H-indole-1-carboxamide |
| 12 | 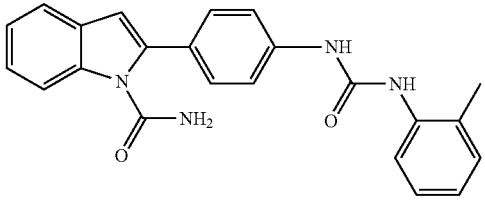 [SMILES: Cc1ccccc1NC(=O)Nc1ccc(-c2cc3ccccc3n2C(N)=O)cc1] | 2-[4-({[(2-methylphenyl)amino]carbonyl}amino)phenyl]-1H-indole-1-carboxamide |
| 13 | 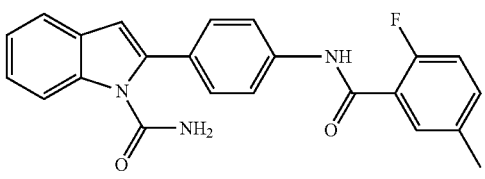 [SMILES: Cc1ccc(F)c(C(=O)Nc2ccc(-c3cc4ccccc4n3C(N)=O)cc2)c1] | 2-{4-[(2-fluoro-5-methylbenzoyl)amino]phenyl}-1H-indole-1-carboxamide |

TABLE 1-continued

List of compound names and structures

| Example | Structure | Compound Name |
|---|---|---|
| 14 | 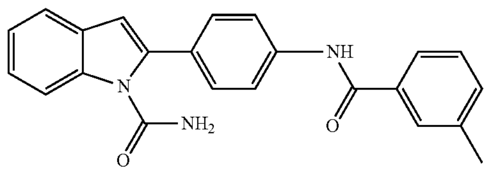 [SMILES: Cc1cccc(C(=O)Nc2ccc(-c3cc4ccccc4n3C(N)=O)cc2)c1] | 2-{4-[(3-methylbenzoyl)amino]phenyl}-1H-indole-1-carboxamide |
| 15 | 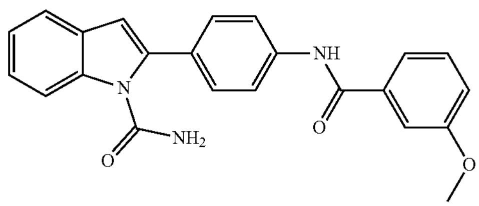 [SMILES: COc1cccc(C(=O)Nc2ccc(-c3cc4ccccc4n3C(N)=O)cc2)c1] | 2-{4-[(3-methoxybenzoyl)amino]phenyl}-1H-indole-1-carboxamide |
| 16 | 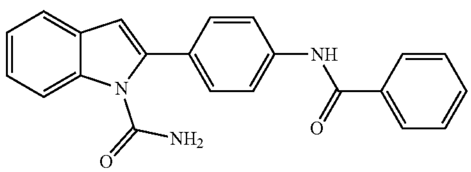 | 2-[4-(benzoylamino)phenyl]-1H-indole-1-carboxamide |
| 17 | 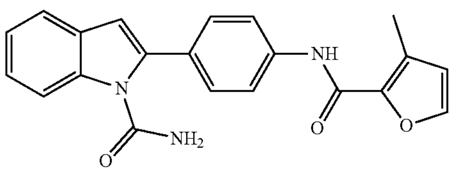 [SMILES: Cc1ccoc1C(=O)Nc1ccc(-c2cc3ccccc3n2C(N)=O)cc1] | 2-{4-[(3-methyl-2-furoyl)amino]phenyl}-1H-indole-1-carboxamide |
| 18 | 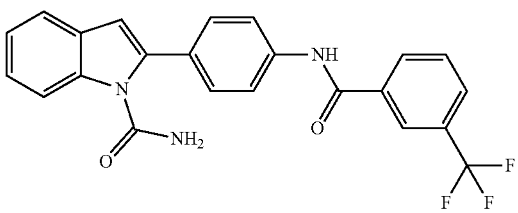 [SMILES: NC(=O)n1c(-c2ccc(NC(=O)c3cccc(C(F)(F)F)c3)cc2)cc2ccccc21] | 2-(4-{[3-(trifluoromethyl)benzoyl]amino}phenyl)-1H-indole-1-carboxamide |
| 19 | 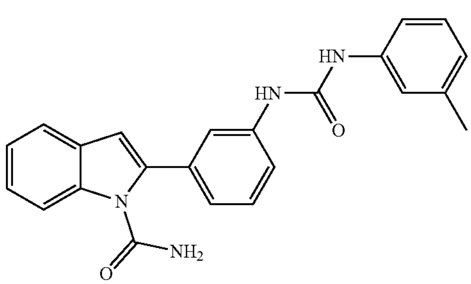 [SMILES: Cc1cccc(NC(=O)Nc2cccc(-c3cc4ccccc4n3C(N)=O)c2)c1] | 2-[3-({[(3-methylphenyl)amino]carbonyl}amino)phenyl]-1H-indole-1-carboxamide |
| 20 | 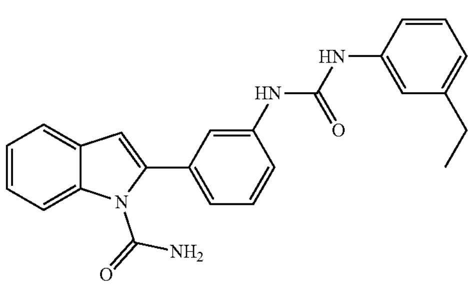 [SMILES: CCc1cccc(NC(=O)Nc2cccc(-c3cc4ccccc4n3C(N)=O)c2)c1] | 2-[3-({[(3-ethylphenyl)amino]carbonyl}amino)phenyl]-1H-indole-1-carboxamide |

TABLE 1-continued

List of compound names and structures

| Example | Structure | Compound Name |
|---|---|---|
| 21 | 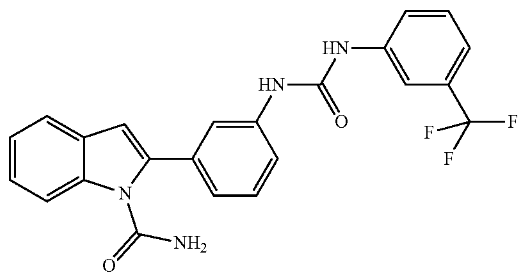 [SMILES: NC(=O)n1c(-c2cccc(NC(=O)Nc3cccc(C(F)(F)F)c3)c2)cc2ccccc21] | 2-{3-[({[3-(trifluoromethyl)phenyl]amino}carbonyl)amino]phenyl}-1H-indole-1-carboxamide |
| 22 | 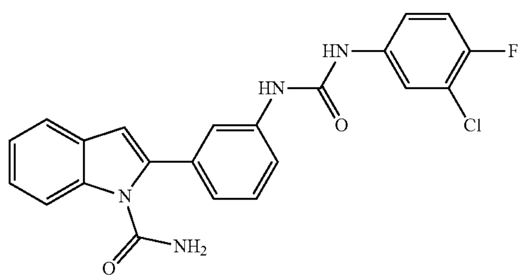 [SMILES: NC(=O)n1c(-c2cccc(NC(=O)Nc3ccc(F)c(Cl)c3)c2)cc2ccccc21] | 2-[3-({[(3-chloro-4-fluorophenyl)amino]carbonyl}amino)phenyl]-1H-indole-1-carboxamide |
| 23 | 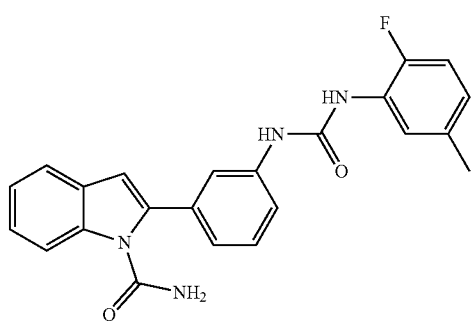 [SMILES: Cc1ccc(F)c(NC(=O)Nc2cccc(-c3cc4ccccc4n3C(N)=O)c2)c1] | 2-[3-({[(2-fluoro-5-methylphenyl)amino]carbonyl}amino)phenyl]-1H-indole-1-carboxamide |
| 24 | 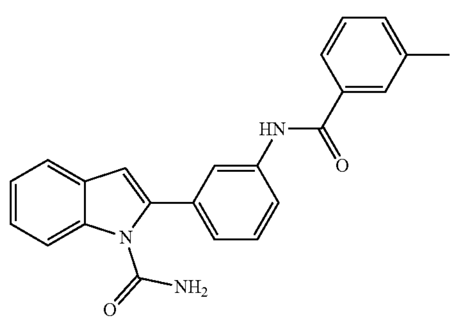 [SMILES: Cc1cccc(C(=O)Nc2cccc(-c3cc4ccccc4n3C(N)=O)c2)c1] | 2-{3-[(3-methylbenzoyl)amino]phenyl}-1H-indole-1-carboxamide |
| 25 | 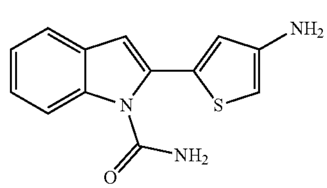 [SMILES: NC(=O)n1c(-c2cc(N)cs2)cc2ccccc21] | 2-(4-amino-2-thienyl)-1H-indole-1-carboxamide |

TABLE 1-continued

List of compound names and structures

| Example | Structure | Compound Name |
|---|---|---|
| 26 | 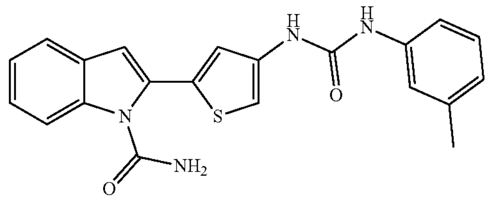 [SMILES: Cc1cccc(NC(=O)Nc2csc(-c3cc4ccccc4n3C(N)=O)c2)c1] | 2-[4-({[(3-methylphenyl)amino]carbonyl}amino)-2-thienyl]-1H-indole-1-carboxamide |
| 27 | 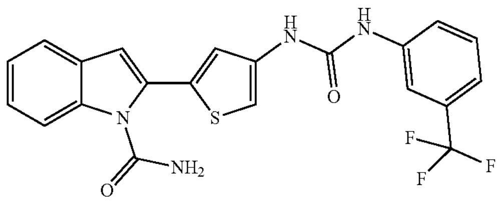 [SMILES: NC(=O)n1c(-c2cc(NC(=O)Nc3cccc(C(F)(F)F)c3)cs2)cc2ccccc21] | 2-{4-[({[3-(trifluoromethyl)phenyl]amino}carbonyl)amino]-2-thienyl}-1H-indole-1-carboxamide |
| 28 | 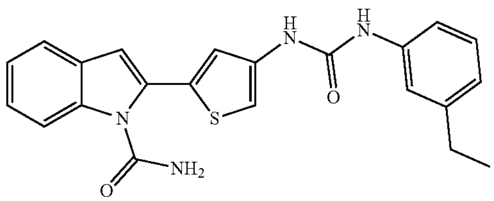 [SMILES: CCc1cccc(NC(=O)Nc2csc(-c3cc4ccccc4n3C(N)=O)c2)c1] | 2-[4-({[(3-ethylphenyl)amino]carbonyl}amino)-2-thienyl]-1H-indole-1-carboxamide |
| 29 | 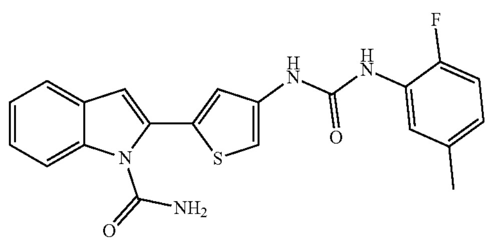 [SMILES: Cc1ccc(F)c(NC(=O)Nc2csc(-c3cc4ccccc4n3C(N)=O)c2)c1] | 2-[4-({[(2-fluoro-5-methylphenyl)amino]carbonyl}amino)-2-thienyl]-1H-indole-1-carboxamide |
| 30 | 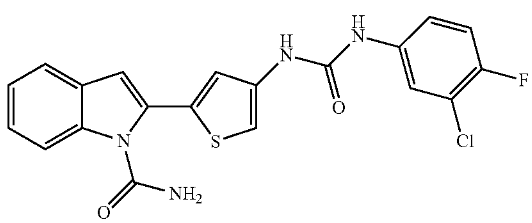 [SMILES: NC(=O)n1c(-c2cc(NC(=O)Nc3ccc(F)c(Cl)c3)cs2)cc2ccccc21] | 2-[4-({[(3-chloro-4-fluorophenyl)amino]carbonyl}amino)-2-thienyl]-1H-indole-1-carboxamide |
| 31 | 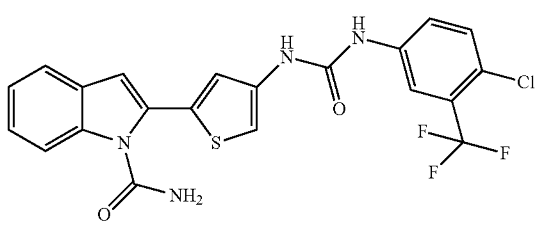 [SMILES: NC(=O)n1c(-c2cc(NC(=O)Nc3ccc(Cl)c(C(F)(F)F)c3)cs2)cc2ccccc21] | 2-{4-[({[4-chloro-3-(trifluoromethyl)phenyl]amino}carbonyl)amino]-2-thienyl}-1H-indole-1-carboxamide |
| 32 | 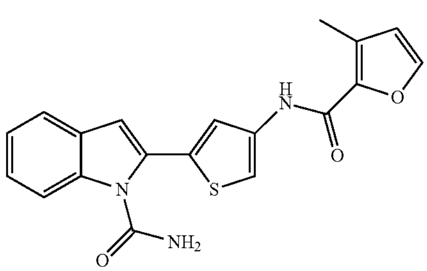 [SMILES: Cc1ccoc1C(=O)Nc1csc(-c2cc3ccccc3n2C(N)=O)c1] | 2-{4-[(3-methyl-2-furoyl)amino]-2-thienyl}-1H-indole-1-carboxamide |

TABLE 1-continued

List of compound names and structures

| Example | Structure | Compound Name |
|---|---|---|
| 33 | 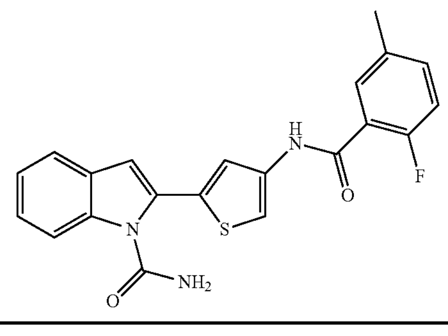 | 2-{4-[(2-fluoro-5-methylbenzoyl)amino]-2-thienyl}-1H-indole-1-carboxamide |

Compounds of formula I are useful as kinase inhibitors. As such, compounds of formula I will be useful for treating diseases related to unregulated tyrosine kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, pterigium, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, age-related macular degeneration, retinopathy of prematurity, etc.

Some compounds of Formula I and some of their intermediates may have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for drop-wise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy.

The present invention is further directed to pharmaceutical compositions comprising a pharmaceutically effective amount of the above-described compounds and a pharmaceutically acceptable carrier or excipient. Such a composition is believed to modulate signal transduction by a protein kinase R, tyrosine kinase, either by inhibition of catalytic activity, affinity to ATP or ability to interact with a substrate.

The present invention relates to compounds capable of regulating and/or modulating tyrosine kinase signal transduction and more particularly receptor and non-receptor tyrosine kinase signal transduction.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered orally, subcutaneously, intravenously, intrathecally or some suitable combination(s) thereof.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738.

For use where a composition for intravenous administration is employed, a suitable daily dosage range for anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

Preferably, the pharmaceutical preparation is in a unit dosage form. In such form, the preparation is subdivided into suitably sized unit doses containing appropriate quantities of the active component, e.g., an effective amount to achieve the desired purpose.

The magnitude of prophylactic or therapeutic dose of a compound of this invention will, of course, vary with the nature of the severity of the condition to be treated and with the particular compound and its route of administration. It will also vary according to the age, weight and response of the individual patient. It is understood that a specific daily dosage amount can simultaneously be both a therapeutically effective amount, e.g., for treatment to slow progression of an existing condition, and a prophylactically effective amount, e.g., for prevention of condition.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In one aspect, the present invention provides a kit comprising a therapeutically effective amount of at least one compound of the present invention, or a pharmaceutically acceptable salt of said compound and a pharmaceutically acceptable carrier, vehicle or diluents, and directions for the use of said kit.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

The present invention concerns also processes for preparing the compounds of Formula I. The compounds of formula I according to the invention can be prepared analogously to conventional methods as understood by the person skilled in the art of synthetic organic chemistry. Synthetic Schemes set forth below, illustrate how the compounds according to the invention can be made.

Scheme 1
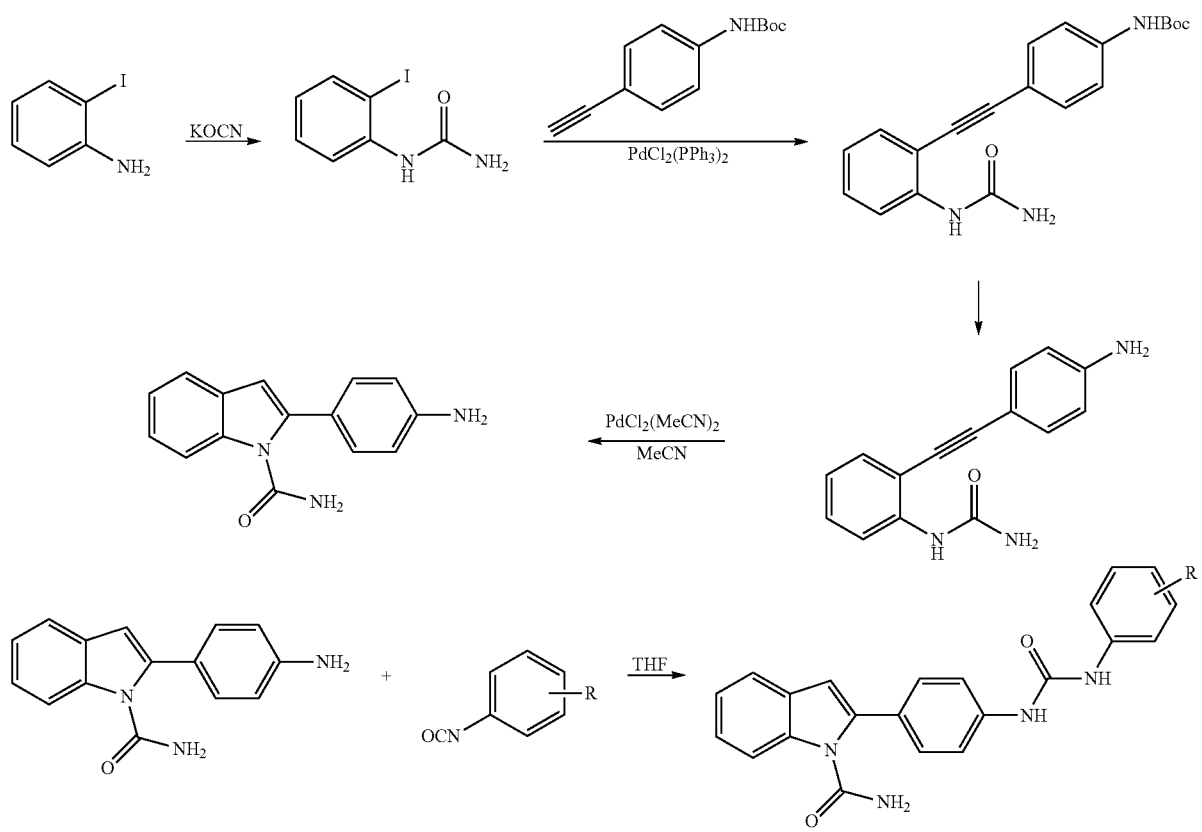
Scheme 2
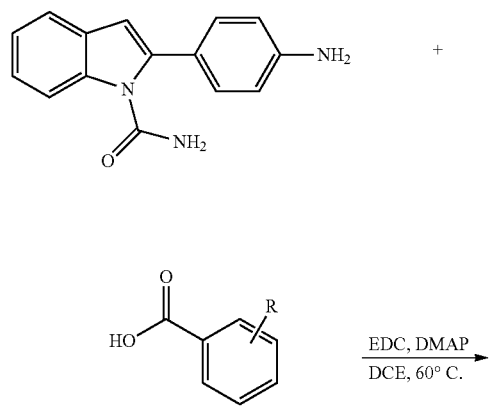
Scheme 3
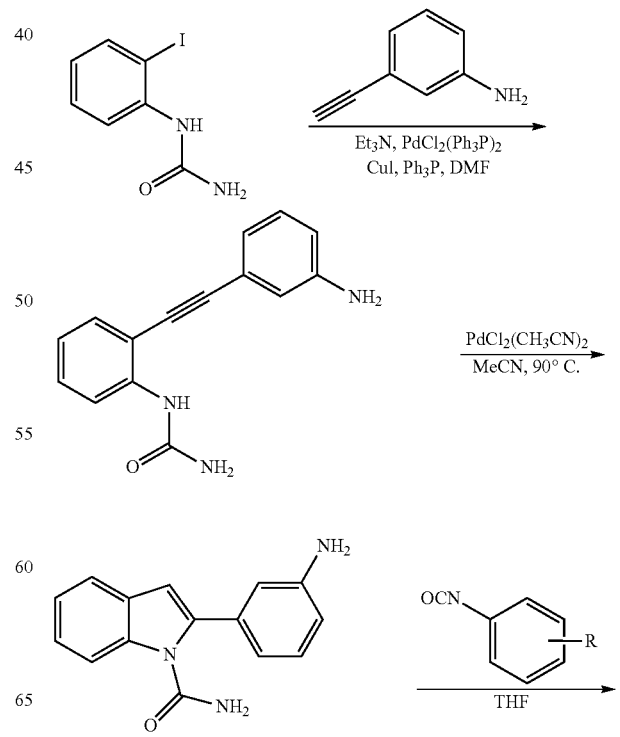

33
-continued
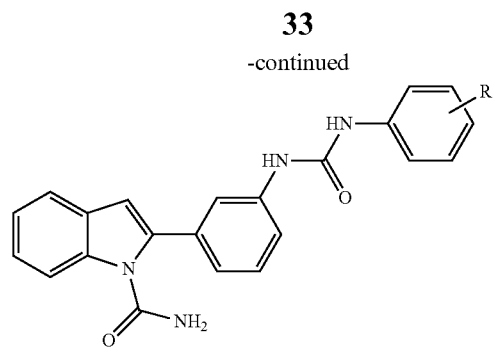
Scheme 4
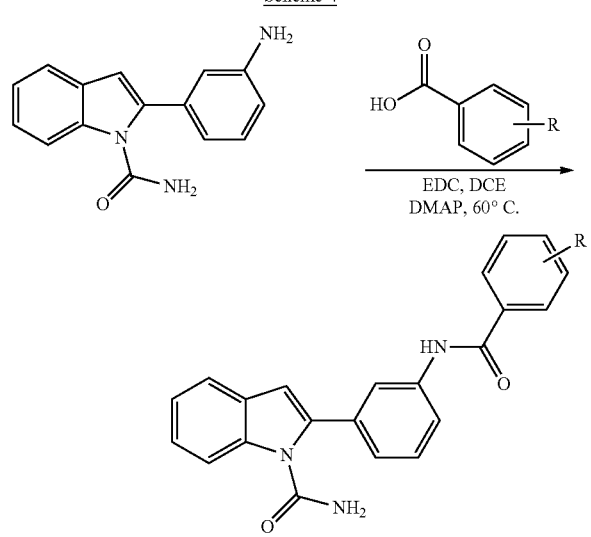
Scheme 5
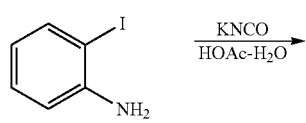
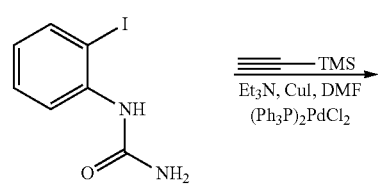
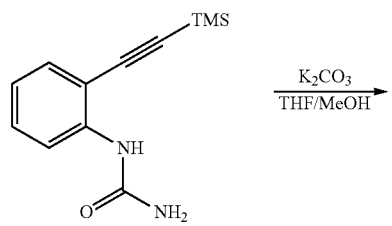
34
-continued
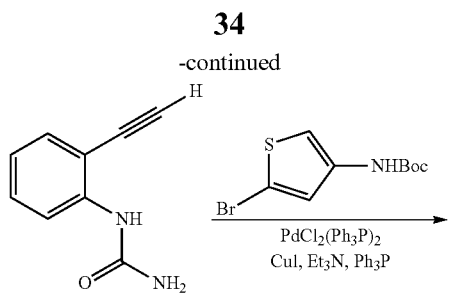
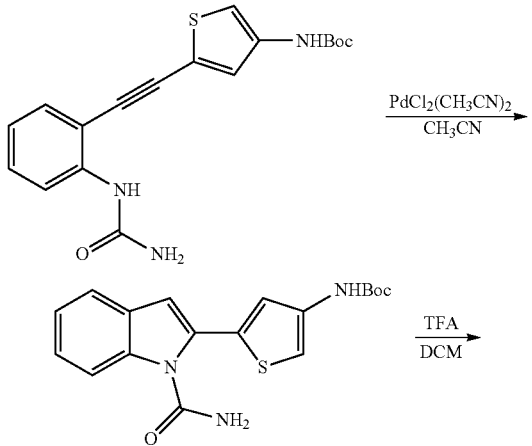
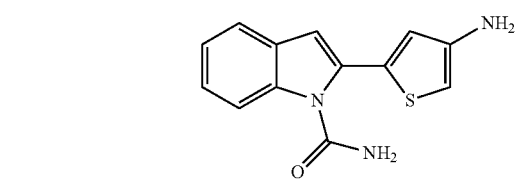
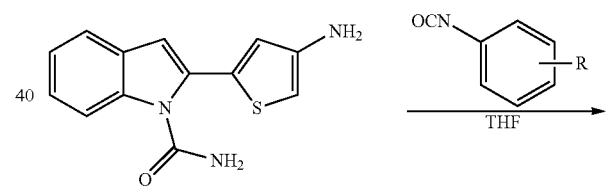
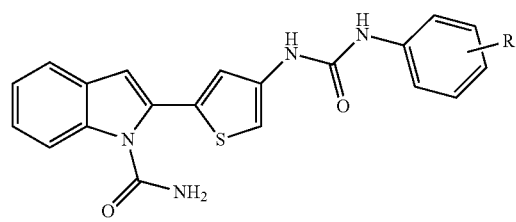
Scheme 6
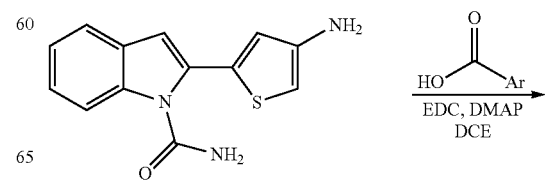

-continued

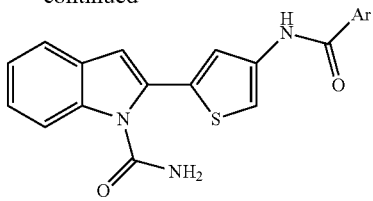

At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I.

The present invention is not to be limited in scope by the exemplified embodiments which are intended as illustrations of single aspects of the invention only. Indeed, various modifications of the invention in addition to those described herein will become apparent to those skilled in the art from the foregoing description.

DETAILED DESCRIPTION OF THE INVENTION

The present invention relates to a method of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders, which comprises administering a pharmaceutical composition comprising a therapeutically effective amount of at least one kinase inhibitor as described herein.

In another aspect, the invention provides the use of at least one kinase inhibitor for the manufacture of a medicament for the treatment of a disease or a condition mediated by tyrosine kinases in a mammal.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of hydrogen $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds is performed according to the following methods; NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by medium pressure liquid chromatography, unless noted otherwise.

Urea Example

Example 1

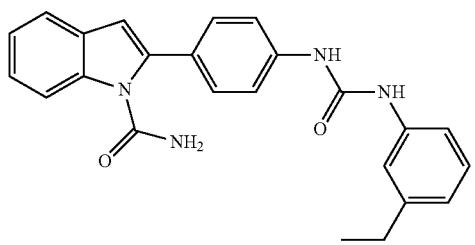

Example 1

2-[4-({[(3-ethylphenyl)amino]carbonyl}amino)phenyl]-1H-indole-1-carboxamide

Synthesis of (2-iodo-phenyl)-urea, Potassium cyanate (22.0 g, 0.271 mol) in water (60 mL) was added to a solution of 2-iodoaniline (50.0 g, 0.228 mol) in acetic acid (125 mL) and water (50 mL) mixture at ambient temperature over 30 min. The resulting mixture was stirred at ambient temperature for 2 hr. The reaction mixture was cooled to 10° C. and filtered the solid and washed with cold water then dried in vacuo to give (2-iodo-phenyl)-urea as light brown solid (57.0 g, 96%).

¹H NMR (200 MHz, DMSO-d⁶) δ 7.90-7.70 (m, 2H), 7.59 (s, 1H), 7.38-7.20 (m, 1H), 6.88-6.65 (m, 1H), 6.34 (br s, 2H).

Synthesis of [4-(2-ureido-phenylethynyl)-phenyl]-carbamic acid tert-butyl ester Copper iodide (0.25 g, 1.2% mol), triphenylphosphine (0.75 g, 2.5% mol) and PdCl₂(PPh₃)₄(9.7 g, 5% mol) was added to a degassed solution of (2-iodo-phenyl)-urea (28.0 g, 0.106 mol), tert-butyl(4-ethynylphenyl)carbamate (23.2 g, 0.106 mol) and triethylamine (54.0 g, 0.534 mo) in DMF (350 mL) at ambient temperature. After stirring at ambient temperature over 30 min, the reaction mixture was heated to 60° C. Heating was continued 2 hr. The mixture was cooled to ambient temperature and stirred for 30 min. The reaction mixture diluted with water (800 mL), extracted with ethyl acetate (3×300 mL) and organic layer was washed with water, saturated NaCl and dried over Na₂SO₄. The solvent was filtered and concentrated in vacuo to give as brown solid. The crude compound purified by column chromatography (20% ethyl acetate/dichloromethane). [4-(2-ureido-phenylethynyl)-phenyl]-carbamic acid tert-butyl ester was obtained as a light brown solid (36.0 g, 98%).

¹H NMR (200 MHz, DMSO-d6) δ 9.60 (s, 1H), 8.10 (d, J=8.0 Hz, 1H), 7.90 (s, 1H), 7.60-7.45 (m, 4H), 7.40 (d, J=7.3 Hz, 1H), 7.28 (t, J=7.3 Hz, 1H), 6.92 (t, J=8.0 Hz, 1H), 6.41 (br s, 2H), 1.50 (s, 9H).

Synthesis of [2-(4-amino-phenylethylnyl)-phenyl]urea[4-(2-ureido-phenylethynyl)-phenyl]-carbamic acid tert-butyl ester (36.0 g) was added portion wise to a solution of trifluoracetic acid (40.0 mL) and dichloromethane (250 mL) at ambient temperature over 20 min. The resulting suspension was heated to 45° C. over 60 min. The reaction mixture was cooled to ambient temperature. The reaction mixture was poured into ice water (2000 ml), stirred for 30 min. The resulting mixture was made basic using ammonium hydroxide. Organic layer was washed with water, saturated NaCl and dried over Na₂SO₄. The solvent was filtered and concentrated in vacuo to give as brown solid (22.0 g, 88%).

¹H NMR (200 MHz, DMSO-d⁶) δ 8.05 (d, J=7.5 Hz, 1H), 7.80 (s, 1H), 7.40-7.17 (m, 4H), 6.90 (t, J=7.5 Hz, 1H), 6.58 (d, J=8.3 Hz, 2H), 6.42 (br s, 2H), 5.55 (br s, 2H).

Synthesis of 2-(4-amino-phenyl)-indole-1-carboxylic acid amide, PdCl₂(MeCN)₂ (4.5 g, 20% mol) was added to a degassed solution of [4-(2-ureido-phenylethynyl)-phenyl]-carbamic acid tert-butyl ester (22.0 g, 0.106 mol) in acetonitrile (450 mL) at ambient temperature. After stirring at ambient temperature over 30 min, the reaction mixture was heated to 80° C. Heating was continued 3 hr. The reaction mixture was cooled to ambient temperature and solvent concentrated in vacuo. The residue taken in ethyl acetate (800 mL) and washed with water, saturated NaCl and dried over Na₂SO₄. The solvent was filtered and concentrated in vacuo to give as brown solid. The crude compound purified by column chromatography (20% ethyl acetate/dichloromethane). 2-(4-amino-phenyl)-indole-1-carboxylic acid amide was obtained as an off white solid (17.0 g, 77%).

HPLC purity: 98.98%

ESI-MS: Calc. for C15H13N3O (M+H)+: 252, found: 252

¹³C NMR (50 MHz, DMSO-d6) δ 153.0, 148.7, 140.4, 136.7, 128.6, 128.5, 122.0, 121.1, 119.7, 119.5, 113.6, 112.2, 103.4.

The reaction mixture of 2-(4-amino-phenyl)-indole-1-carboxylic acid amide (125.5 mg, 0.5 mmol, 1 eq) and 3-ethylphenyl isocyanate (0.073 mL, 1 eq) in anhydrous THF (4 mL) was stirred at room temperature for 2 hours. It was then diluted with ethyl acetate, washed sequentially with aqueous NH₄Cl, saturated aqueous NaHCO₃, brine, and dried with anhydrous sodium sulfate. The upper liquor was decanted, concentrated, and the solid residue was triturated with EtOAC-Hex (1:1). 2-[4-({[(3-ethylphenyl)amino]carbonyl}amino)phenyl]-1H-indole-1-carboxamide was obtained as white solid upon filtration in amount of 156 mg (78%).

¹H NMR (DMSO-d₆) δ: 8.79 (s, 1H), 8.65 (s, 1H), 7.89 (br. s., 1H), 7.74 (br. s., 1H), 7.70 (d, J=8.2 Hz, 1H), 7.58 (d, J=7.8 Hz, 1H), 7.53 (d, J=8.5 Hz, 2H), 7.45 (d, J=8.5 Hz, 2H), 7.34 (s, 1H), 7.13-7.28 (m, 4H), 6.84 (d, J=7.3 Hz, 1H), 6.72 (s, 1H), 2.58 (q, J=7.5 Hz, 2H), 1.19 (t, J=7.6 Hz, 3H).

The following Examples were synthesized according to the procedure described in Example 1.

Example 2

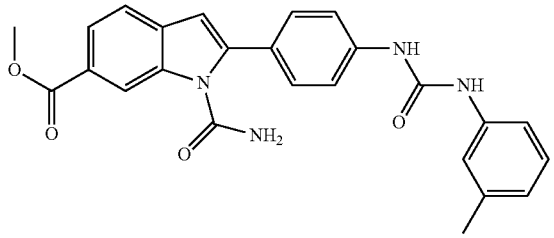 [SMILES: COC(=O)c1ccc2cc(-c3ccc(NC(=O)Nc4cccc(C)c4)cc3)n(C(N)=O)c2c1]

methyl 1-(aminocarbonyl)-2-[4-({[(3-methylphenyl)amino]carbonyl}amino)phenyl]-1H-indole-6-carboxylate ¹H NMR (DMSO-d₆) δ: 8.85 (s, 1H), 8.65 (s, 1H), 8.34 (s, 1H), 8.07 (br. s., 1H), 7.97 (br. s., 1H), 7.78 (dd, J=8.4, 1.3 Hz, 1H), 7.68 (d, J=8.2 Hz, 1H), 7.54-7.58 (m, 2H), 7.50 (d, J=8.8 Hz, 2H), 7.32 (s, 1H), 7.25 (d, J=8.2 Hz, 1H), 7.17 (t, J=7.8 Hz, 1H), 6.85 (s, 1H), 6.81 (d, J=7.3 Hz, 1H), 3.89 (s, 3H), 2.29 (s, 3H).

Example 3

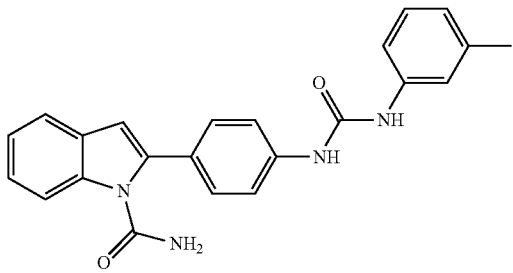 [SMILES: Cc1cccc(NC(=O)Nc2ccc(-c3cc4ccccc4n3C(N)=O)cc2)c1]

2-[4-({[(3-methylphenyl)amino]carbonyl}amino)phenyl]-1H-indole-1-carboxamide

¹H NMR (DMSO-d₆) δ: 8.80 (s, 1H), 8.64 (s, 1H), 7.86 (br. s., 1H), 7.76 (br. s., 1H), 7.70 (d, J=8.2 Hz, 1H), 7.58 (d, J=7.3 Hz, 1H), 7.49-7.56 (m, 2H), 7.41-7.49 (m, 2H), 7.31 (s, 1H), 7.11-7.27 (m, 4H), 6.80 (d, J=7.3 Hz, 1H), 6.72 (s, 1H), 2.29 (s, 3H).

Example 4

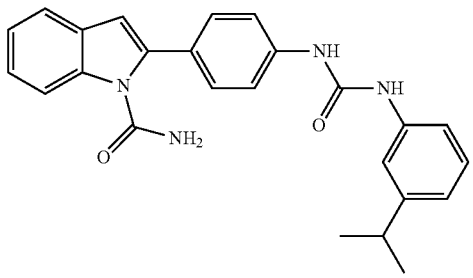 [SMILES: CC(C)c1cccc(NC(=O)Nc2ccc(-c3cc4ccccc4n3C(N)=O)cc2)c1]

2-[4-({[(3-isopropylphenyl)amino]carbonyl}amino)phenyl]-1H-indole-1-carboxamide

¹H NMR (DMSO-d$_6$) δ: 8.78 (s, 1H), 8.66 (s, 1H), 7.89 (br. s., 1H), 7.74 (br. s., 1H), 7.70 (d, J=8.2 Hz, 1H), 7.58 (d, J=7.6 Hz, 1H), 7.52-7.55 (m, 2H), 7.43-7.47 (m, 2H), 7.35 (t, J=1.6 Hz, 1H), 7.26-7.29 (m, 1H), 7.23 (ddd, J=8.3, 7.3, 1.2 Hz, 1H), 7.20 (t, J=7.8 Hz, 1H), 7.13-7.17 (m, 1H), 6.87 (d, J=7.6 Hz, 1H), 6.72 (s, 1H), 2.85 (dquin, J=13.8, 6.8 Hz, 1H), 1.21 (d, J=6.7 Hz, 6H).

Example 5

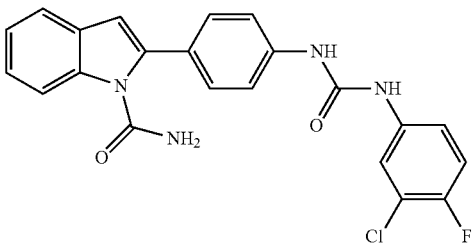 [SMILES: NC(=O)n1c(-c2ccc(NC(=O)Nc3ccc(F)c(Cl)c3)cc2)cc2ccccc21]

2-[4-({[(3-chloro-4-fluorophenyl)amino]carbonyl}amino)phenyl]-1H-indole-1-carboxamide ¹H NMR (DMSO-d$_6$) δ: 8.92 (s, 1H), 8.91 (s, 1H), 7.89 (br. s., 1H), 7.82 (dd, J=6.6, 2.2 Hz, 1H), 7.75 (br. s., 1H), 7.70 (d, J=8.5 Hz, 1H), 7.58 (d, J=7.6 Hz, 1H), 7.52-7.55 (m, 2H), 7.44-7.48 (m, 2H), 7.31-7.37 (m, 2H), 7.23 (ddd, J=8.2, 7.0, 1.2 Hz, 1H), 7.14-7.17 (m, 1H), 6.73 (s, 1H).

Example 6

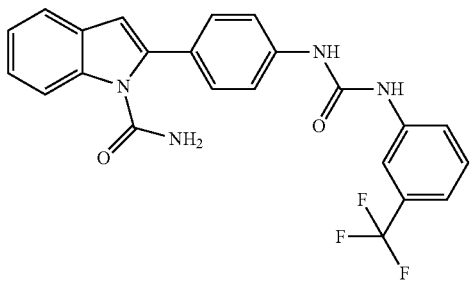 [SMILES: NC(=O)n1c(-c2ccc(NC(=O)Nc3cccc(C(F)(F)F)c3)cc2)cc2ccccc21]

2-{4-[({[3-(trifluoromethyl)phenyl]amino}carbonyl)amino]phenyl}-1H-indole-1-carboxamide ¹H NMR (DMSO-d$_6$) δ: 9.10 (s, 1H), 8.94 (s, 1H), 8.03 (s, 1H), 7.89 (br. s., 1H), 7.76 (br. s., 1H), 7.70 (d, J=8.2 Hz, 1H), 7.50-7.61 (m, 5H), 7.45-7.49 (m, 2H), 7.32 (d, J=7.6 Hz, 1H), 7.23 (ddd, J=8.2, 7.0, 1.2 Hz, 1H), 7.14-7.17 (m, 1H), 6.73 (s, 1H).

Example 7

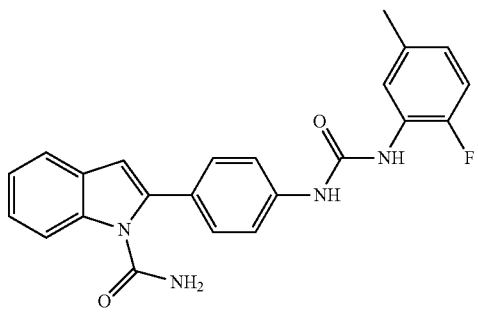 [SMILES: Cc1ccc(F)c(NC(=O)Nc2ccc(-c3cc4ccccc4n3C(N)=O)cc2)c1]

2-[4-({[(2-fluoro-5-methylphenyl)amino]carbonyl}amino)phenyl]-1H-indole-1-carboxamide ¹H NMR (DMSO-d$_6$) δ: 9.20 (s, 1H), 8.53 (d, J=2.3 Hz, 1H), 8.01 (dd, J=7.9, 1.8 Hz, 1H), 7.86 (br. s., 1H), 7.77 (br. s., 1H), 7.70 (d, J=8.2 Hz, 1H), 7.43-7.61 (m, 5H), 7.23 (td, J=7.6, 1.2 Hz, 1H), 7.06-7.19 (m, 2H), 6.77-6.85 (m, 1H), 6.73 (s, 1H), 2.28 (s, 3H)

Example 8

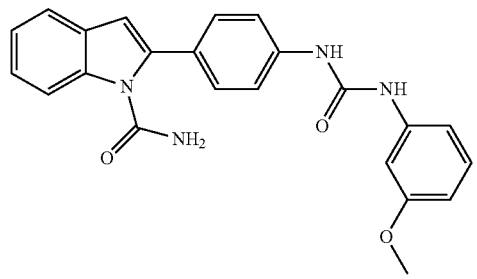

2-[4-({[(3-methoxyphenyl)amino]carbonyl}amino)phenyl]-1H-indole-1-carboxamide

¹H NMR (DMSO-d$_6$) δ: 8.80 (s, 1H), 8.73 (s, 1H), 7.88 (br. s., 1H), 7.74 (br. s., 1H), 7.70 (d, J=8.5 Hz, 1H), 7.58 (d, J=7.6 Hz, 1H), 7.51-7.55 (m, 2H), 7.44-7.47 (m, 2H), 7.23 (ddd, J=8.1, 7.3, 1.3 Hz, 1H), 7.17-7.21 (m, 2H), 7.13-7.17 (m, 1H), 6.95 (dd, J=8.2, 1.2 Hz, 1H), 6.72 (s, 1H), 6.55-6.58 (m, 1H), 3.74 (s, 3H)

Example 9

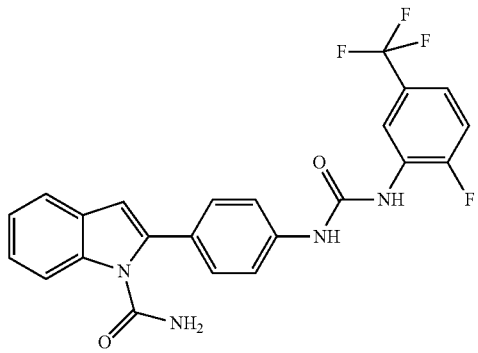 [SMILES: NC(=O)n1c(-c2ccc(NC(=O)Nc3cc(C(F)(F)F)ccc3F)cc2)cc2ccccc21]

2-{4-[({[2-fluoro-5-(trifluoromethyl)phenyl]amino}carbonyl)amino]phenyl}-1H-indole-1-carboxamide ¹H NMR (DMSO-d₆) δ: 9.32 (s, 1H), 8.95 (d, J=2.6 Hz, 1H), 8.64 (dd, J=7.3, 2.1 Hz, 1H), 7.86 (br. s., 1H), 7.80 (br. s., 1H), 7.71 (d, J=8.2 Hz, 1H), 7.46-7.61 (m, 6H), 7.37-7.44 (m, 1H), 7.24 (ddd, J=8.1, 7.1, 1.2 Hz, 1H), 7.12-7.19 (m, 1H), 6.74 (s, 1H).

Example 10

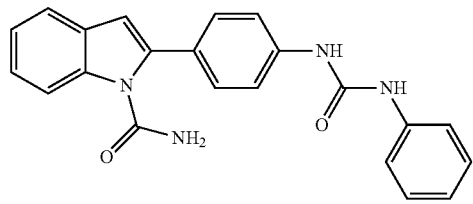 [SMILES: NC(=O)n1c(-c2ccc(NC(=O)Nc3ccccc3)cc2)cc2ccccc21]

2-{4-[(anilinocarbonyl)amino]phenyl}-1H-indole-1-carboxamide

¹H NMR (DMSO-d₆) δ: 8.81 (s, 1H), 8.71 (s, 1H), 7.88 (br. s., 1H), 7.74 (br. s., 1H), 7.70 (d, J=8.2 Hz, 1H), 7.58 (d, J=7.6 Hz, 1H), 7.54 (d, J=7.6 Hz, 2H), 7.46 (t, J=7.9 Hz, 4H), 7.29 (t, J=7.3 Hz, 2H), 7.23 (t, J=7.6 Hz, 1H), 7.13-7.17 (m, 1H), 6.98 (t, J=7.2 Hz, 1H), 6.72 (s, 1H).

Example 11

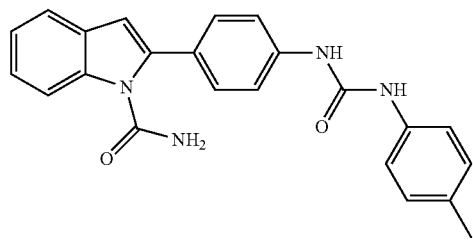 [SMILES: Cc1ccc(NC(=O)Nc2ccc(-c3cc4ccccc4n3C(N)=O)cc2)cc1]

2-[4-({[(4-methylphenyl)amino]carbonyl}amino)phenyl]-1H-indole-1-carboxamide

¹H NMR (DMSO-d₆) δ: 8.76 (s, 1H), 8.60 (s, 1H), 7.88 (br. s., 1H), 7.74 (br. s., 1H), 7.70 (d, J=8.2 Hz, 1H), 7.58 (d, J=7.9 Hz, 1H), 7.50-7.54 (m, 2H), 7.43-7.46 (m, 2H), 7.33-7.37 (m, 2H), 7.23 (ddd, J=8.3, 7.3, 1.2 Hz, 1H), 7.13-7.17 (m, 1H), 7.10 (d, J=8.2 Hz, 2H), 6.72 (s, 1H), 2.25 (s, 3H).

Example 12

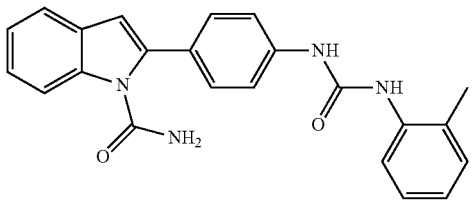

2-[4-({[(2-methylphenyl)amino]carbonyl}amino)phenyl]-1H-indole-1-carboxamide

¹H NMR (DMSO-d₆) δ: 9.17 (s, 1H), 7.98 (s, 1H), 7.89 (br. s., 1H), 7.85 (d, J=7.9 Hz, 1H), 7.74 (br. s., 1H), 7.70 (d, J=8.2 Hz, 1H), 7.58 (d, J=7.6 Hz, 1H), 7.55 (d, J=8.8 Hz, 2H), 7.46 (d, J=8.8 Hz, 2H), 7.21-7.25 (m, 1H), 7.13-7.20 (m, 3H), 6.96 (t, J=7.3 Hz, 1H), 6.72 (s, 1H), 2.26 (s, 3H).

Representative Procedure

Amide Example

Example 14

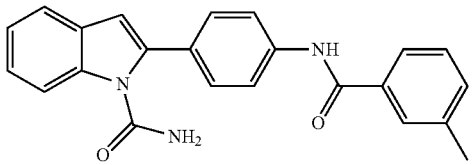

2-{4-[(3-methylbenzoyl)amino]phenyl}-1H-indole-1-carboxamide

To the solution of 2-(4-amino-phenyl)-indole-1-carboxylic acid amide (125.5 mg, 0.5 mmol, 1 eq) and m-toluic acid (68.8 mg, 0.5 mmol, 1 eq) in anhydrous DCE (4 mL) was added DMAP (12.2 mg, 0.2 eq) and EDC (115.2 mg, 1.2 eq). The reaction mixture was heated at 60° C. for 1.5 hours. It was then cooled to room temperature, diluted with ethyl acetate, washed subsequently with aqueous NH₄Cl, saturated aqueous NaHCO₃, brine, and lastly dried with anhydrous sodium sulfate. The upper liquor was decanted, concentrated, and the solid residue was treated with EtOAC-Hex(2:1) with stirring. 2-{4-[(3-methylbenzoyl)amino]phenyl}-1H-indole-1-carboxamide was obtained as slightly brown solid upon filtration in amount of 165 mg (89%).

¹H NMR (DMSO-d₆) δ: 10.33 (s, 1H), 7.81-7.94 (m, 4H), 7.75-7.81 (m, 2H), 7.71 (d, J=8.2 Hz, 1H), 7.60 (d, J=7.8 Hz,

1H), 7.52 (d, J=8.7 Hz, 2H), 7.41-7.46 (m, 2H), 7.24 (t, J=7.7 Hz, 1H), 7.14-7.19 (m, 1H), 6.77 (s, 1H), 2.42 (s, 3H).

The following Examples were synthesized according to the procedure described in Example 14.

Example 13

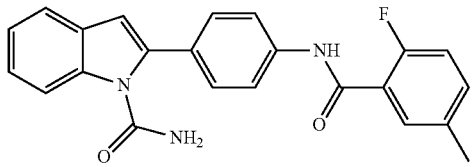 [SMILES: Cc1cccc(C(=O)Nc2ccc(-c3cc4ccccc4n3C(N)=O)cc2)c1]

2-{4-[(2-fluoro-5-methylbenzoyl)amino]phenyl}-1H-indole-1-carboxamide $^1$H NMR (DMSO-$d_6$) δ: 10.50 (s, 1H), 7.89 (br. s., 1H), 7.74-7.83 (m, 3H), 7.71 (d, J=8.2 Hz, 1H), 7.60 (d, J=7.9 Hz, 1H), 7.52 (d, J=8.5 Hz, 2H), 7.48 (dd, J=6.3, 1.3 Hz, 1H), 7.36-7.41 (m, 1H), 7.22-7.27 (m, 2H), 7.15-7.18 (m, 1H), 6.77 (s, 1H), 2.36 (s, 3H)

Example 15

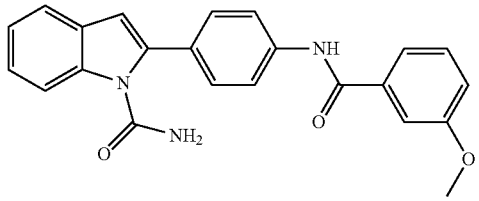 [SMILES: COc1cccc(C(=O)Nc2ccc(-c3cc4ccccc4n3C(N)=O)cc2)c1]

2-{4-[(3-methoxybenzoyl)amino]phenyl}-1H-indole-1-carboxamide $^1$H NMR (DMSO-$d_6$) δ: 10.34 (s, 1H), 7.90 (br. s., 1H), 7.86 (d, J=8.5 Hz, 2H), 7.77 (br. s., 1H), 7.72 (d, J=8.2 Hz, 1H), 7.60 (d, J=7.9 Hz, 1H), 7.56 (d, J=7.6 Hz, 1H), 7.50-7.54 (m, 3H), 7.47 (t, J=7.8 Hz, 1H), 7.23-7.27 (m, 1H), 7.14-7.20 (m, 2H), 6.78 (s, 1H), 3.85 (s, 3H).

Example 16

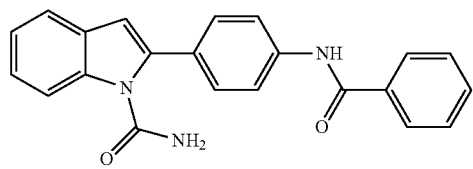 [SMILES: NC(=O)n1c(-c2ccc(NC(=O)c3ccccc3)cc2)cc2ccccc21]

2-[4-(benzoylamino)phenyl]-1H-indole-1-carboxamide $^1$H NMR (DMSO-$d_6$) δ: 10.38 (s, 1H), 7.98 (d, J=7.0 Hz, 2H), 7.90 (br. s., 1H), 7.87 (d, J=8.5 Hz, 2H), 7.77 (br. s., 1H), 7.72 (d, J=8.2 Hz, 1H), 7.59-7.63 (m, 2H), 7.51-7.58 (m, 4H), 7.22-7.27 (m, 1H), 7.15-7.18 (m, 1H), 6.78 (s, 1H).

Example 17

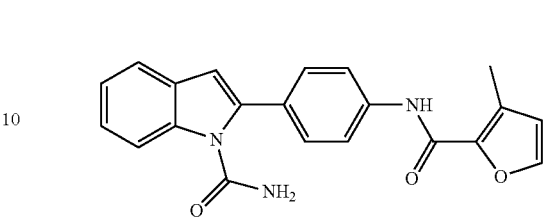

2-{4-[(3-methyl-2-furoyl)amino]phenyl}-1H-indole-1-carboxamide $^1$H NMR (DMSO-$d_6$) δ: 10.17 (s, 1H), 7.90 (br. s., 1H), 7.84-7.87 (m, 2H), 7.81 (d, J=1.5 Hz, 1H), 7.78 (br. s., 1H), 7.70 (d, J=8.2 Hz, 1H), 7.59 (d, J=7.9 Hz, 1H), 7.47-7.50 (m, 2H), 7.24 (ddd, J=8.1, 7.1, 1.2 Hz, 1H), 7.14-7.18 (m, 1H), 6.76 (s, 1H), 6.61 (d, J=1.5 Hz, 1H), 2.36 (s, 3H)

Example 18

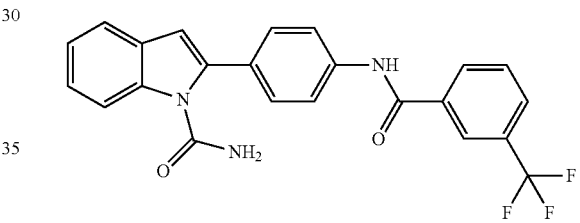

2-(4-{[3-(trifluoromethyl)benzoyl]amino}phenyl)-1H-indole-1-carboxamide $^1$H NMR (DMSO-$d_6$) δ: 10.60 (s, 1H), 8.32 (s, 1H), 8.29 (d, J=7.6 Hz, 1H), 7.99 (d, J=7.6 Hz, 1H), 7.91 (br. s., 1H), 7.86 (d, J=8.5 Hz, 2H), 7.77-7.84 (m, 2H), 7.72 (d, J=8.2 Hz, 1H), 7.60 (d, J=7.6 Hz, 1H), 7.55 (d, J=8.5 Hz, 2H), 7.25 (t, J=7.8 Hz, 1H), 7.15-7.19 (m, 1H), 6.79 (s, 1H).

Example 24

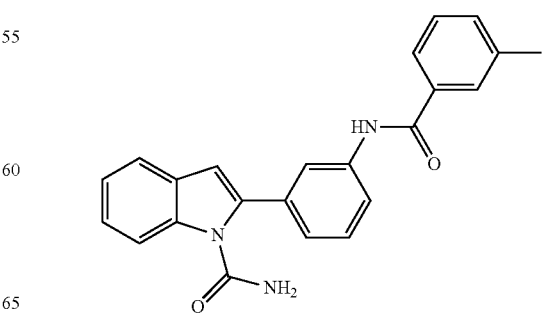

2-{3-[(3-methylbenzoyl)amino]phenyl}-1H-indole-1-carboxamide

To the solution of 2-(3-aminophenyl)-1H-indole-1-carboxamide (50.2 mg, 0.2 mmol, 1 eq) and m-toluic acid (27.5 mg, 1 eq) in anhydrous DCE (2 mL) was added 4-(dimethylamino)pyridine (4.9 mg, 0.2 eq) and N-(3-dimethylaminopropyl)-N'-ethylcarbodiimide hydrochloride (46.1 mg, 1.2 eq). After the reaction was stirred at 60° C. for 1 hour, it was diluted with ethyl acetate, washed sequentially with aqueous ammonium chloride, saturated aqueous sodium bicarbonate, brine, and lastly dried with anhydrous sodium sulfate. The upper clear solution was decanted, concentrated, and the oily residue was subject to a gradient column chromatography (EtOAc-Hex 1:10 to 1:1) to give 2-{3-[(3-methylbenzoyl)amino]phenyl}-1H-indole-1-carboxamide as a clear oil which turned into a white foam in vacuo in amount of 34 mg.

$^1$H NMR (DMSO-$d_6$) δ: 10.34 (s, 1H), 8.06 (t, J=1.8 Hz, 1H), 7.87 (br. s., 1H), 7.75-7.83 (m, 4H), 7.73 (d, J=7.9 Hz, 1H), 7.63 (d, J=7.6 Hz, 1H), 7.40-7.46 (m, 3H), 7.24-7.29 (m, 2H), 7.15-7.20 (m, 1H), 6.77 (s, 1H), 2.41 (s, 3H)

Representative Procedure

Urea Example

Example 19

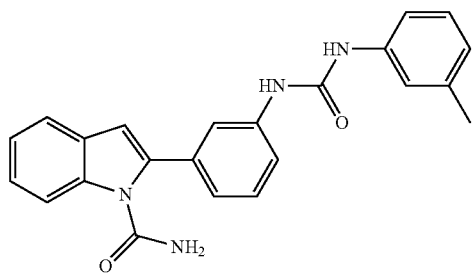 [SMILES: Cc1cccc(NC(=O)Nc2cccc(-c3cc4ccccc4n3C(N)=O)c2)c1]

2-[3-({[(3-methylphenyl)amino]carbonyl}amino)phenyl]-1H-indole-1-carboxamide

To the nitrogen degassed solution of 1-(2-iodophenyl)urea (1.31 g, 5 mmol, 1 eq), 3-ethynylaniline (0.8 mL, 1.5 eq), triphenylphosphine (32.8 mg, 0.025 eq), and triethylamine (2.1 mL, 3 eq) in anhydrous DMF (12.5 mL) was added copper(I) iodide (190.4 mg, 0.2 eq) and bis(triphenylphosphine)palladium(II) dichloride (351 mg, 0.1 eq). After the reaction mixture was stirred at room temperature for 10 minutes, it was diluted with ethyl acetate, washed sequentially with aqueous ammonium chloride, saturated aqueous sodium bicarbonate, brine, and lastly dried with anhydrous sodium sulfate. The upper solution was decanted, concentrated, and the solid mixture was subject to a gradient column chromatography (EtOAc-Hex 1:2 to MeOH-EtOAc 1:9) to give 1-{2-[(3-aminophenyl)ethynyl]phenyl}urea as a brown solid in amount of 1.26 g.

$^1$H NMR (DMSO-$d_6$) δ: 8.07 (d, J=8.2 Hz, 1H), 7.91 (s, 1H), 7.41 (dd, J=7.6, 1.5 Hz, 1H), 7.25-7.29 (m, 1H), 7.07 (t, J=7.8 Hz, 1H), 6.95 (td, J=7.5, 1.2 Hz, 1H), 6.80-6.82 (m, 1H), 6.78 (d, J=7.6 Hz, 1H), 6.60-6.63 (m, 1H), 6.44 (br. s., 2H), 5.24 (s, 2H).

The mixture of 1-{2-[(3-aminophenyl)ethynyl]phenyl}urea (1.25 g, 5 mmol, 1 eq) in anhydrous CH$_3$CN (35 mL) was bubbled with anhydrous nitrogen for about 15 minutes, followed by the addition of bis(acetonitrile)dichloropalladium (II) (259 mg, 0.2 eq). The resulting mixture was heated at 90° C. for 2 hours, then another batch of bis(acetonitrile)dichloropalladium (II) (259 mg, 0.2 eq) was added and the reaction was continued at 90° C. for 3 hours. The reaction mixture was then concentrated under reduced pressure to remove some of the acetonitrile solvent and the residue was taken into ethyl acetate. The organic solvent mixture was washed with water, brine, and dried with anhydrous sodium sulfate. The solvent mixture was filtered, the filtrate was isolated and concentrated, and the resulting solid residue was subject to a gradient column chromatography [from dichloromethane to MeOH-DCM (1:20)] to yield 2-(3-aminophenyl)-1H-indole-1-carboxamide as a yellow solid (184 mg).

$^1$H NMR (DMSO-$d_6$) δ: 7.82 (br. s., 1H), 7.70 (d, J=8.2 Hz, 1H), 7.57 (d, J=7.6 Hz, 2H), 7.22 (t, J=7.8 Hz, 1H), 7.12-7.16 (m, 1H), 7.07 (t, J=7.6 Hz, 1H), 6.75 (t, J=1.9 Hz, 1H), 6.67 (d, J=7.3 Hz, 1H), 6.63 (s, 1H), 6.56 (dd, J=7.9, 1.5 Hz, 1H), 5.19 (s, 2H)

To the solution of 2-(3-aminophenyl)-1H-indole-1-carboxamide (50.2 mg, 0.2 mmol, 1 eq) in anhydrous THF (2 mL) was added m-tolyl isocyanate (25 μL, 1 eq) and the reaction solution was stirred at room temperature for one hour. It was then diluted with ethyl acetate, washed with aqueous ammonium chloride, saturated aqueous sodium bicarbonate, brine, and lastly dried with anhydrous sodium sulfate. The upper solution was decanted, concentrated and the oily residue was treated with small amount of dichloromethane. The white solid appeared during this process was filtered to yield 2-[3-({[(3-methylphenyl)amino]carbonyl}amino)phenyl]-1H-indole-1-carboxamide in amount of 36 mg.

$^1$H NMR (DMSO-$d_6$) δ: 8.77 (s, 1H), 8.61 (s, 1H), 7.89 (br. s., 1H), 7.81 (br. s., 1H), 7.72 (d, J=8.2 Hz, 1H), 7.66 (t, J=1.8 Hz, 1H), 7.62 (d, J=7.6 Hz, 1H), 7.46 (dd, J=8.2, 1.2 Hz, 1H), 7.35 (t, J=7.9 Hz, 1H), 7.32 (s, 1H), 7.22-7.28 (m, 2H), 7.13-7.19 (m, 3H), 6.80 (d, J=7.3 Hz, 1H), 6.76 (s, 1H), 2.28 (s, 3H).

Example 20

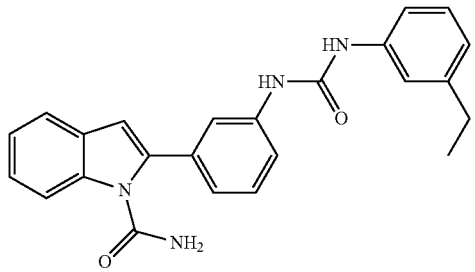 [SMILES: CCc1cccc(NC(=O)Nc2cccc(-c3cc4ccccc4n3C(N)=O)c2)c1]

2-[3-({[(3-ethylphenyl)amino]carbonyl}amino)phenyl]-1H-indole-1-carboxamide

To the solution of 2-(3-aminophenyl)-1H-indole-1-carboxamide (50.2 mg, 0.2 mmol, 1 eq) in anhydrous THF (2 mL) was added 3-ethylphenyl isocyanate (29 μL, 1 eq) and the reaction solution was stirred at room temperature for one hour. It was then diluted with ethyl acetate, washed with aqueous ammonium chloride, saturated aqueous sodium bicarbonate, brine, and lastly dried with anhydrous sodium sulfate. The upper solution was decanted, concentrated and the oily residue was subject to a gradient column chromatography (from EtOAc-Hex 1:2 to MeOH-EtOAc 1:10). The product fractions were collected, concentrated, and the solid residue was triturated with EtOAc-Hex (1:1) to give 2-[3-({[(3-ethylphenyl)amino]carbonyl}amino)phenyl]-1H-indole-1-carboxamide as white solid upon filtration in amount of 32 mg.

$^1$H NMR (DMSO-d$_6$) δ: 8.76 (s, 1H), 8.63 (s, 1H), 7.89 (br. s., 1H), 7.81 (br. s., 1H), 7.72 (d, J=8.2 Hz, 1H), 7.65 (t, J=1.8 Hz, 1H), 7.62 (d, J=7.6 Hz, 1H), 7.46 (dd, J=8.1, 1.0 Hz, 1H), 7.32-7.37 (m, 2H), 7.24-7.28 (m, 2H), 7.12-7.20 (m, 3H), 6.83 (d, J=7.3 Hz, 1H), 6.76 (s, 1H), 2.58 (q, J=7.4 Hz, 2H), 1.18 (t, J=7.5 Hz, 3H).

Example 21

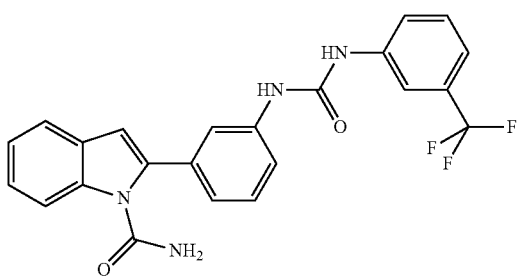 [SMILES: NC(=O)n1c(-c2cccc(NC(=O)Nc3cccc(C(F)(F)F)c3)c2)cc2ccccc21]

2-{3-[({[3-(trifluoromethyl)phenyl]amino}carbonyl)amino]phenyl}-1H-indole-1-carboxamide $^1$H NMR (DMSO-d$_6$) δ: 9.07 (s, 1H), 8.92 (s, 1H), 8.03 (s, 1H), 7.89 (br. s., 1H), 7.84 (br. s., 1H), 7.72 (d, J=8.2 Hz, 1H), 7.68 (t, J=1.8 Hz, 1H), 7.62 (d, J=7.9 Hz, 1H), 7.58 (d, J=8.8 Hz, 1H), 7.52 (t, J=7.9 Hz, 1H), 7.46-7.48 (m, 1H), 7.37 (t, J=7.9 Hz, 1H), 7.32 (d, J=7.6 Hz, 1H), 7.24-7.28 (m, 1H), 7.15-7.19 (m, 2H), 6.77 (s, 1H).

Example 22

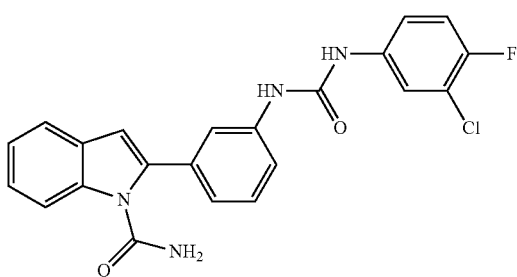 [SMILES: NC(=O)n1c(-c2cccc(NC(=O)Nc3ccc(F)c(Cl)c3)c2)cc2ccccc21]

2-[3-({[(3-chloro-4-fluorophenyl)amino]carbonyl}amino)phenyl]-1H-indole-1-carboxamide $^1$H NMR (DMSO-d$_6$) δ: 8.90 (s, 1H), 8.89 (s, 1H), 7.89 (br. s., 1H), 7.80-7.85 (m, 2H), 7.71 (d, J=8.5 Hz, 1H), 7.67 (t, J=1.8 Hz, 1H), 7.61 (d, J=7.9 Hz, 1H), 7.43-7.46 (m, 1H), 7.30-7.38 (m, 3H), 7.26 (ddd, J=8.2, 7.0, 1.2 Hz, 1H), 7.15-7.19 (m, 2H), 6.76 (s, 1H).

Example 23

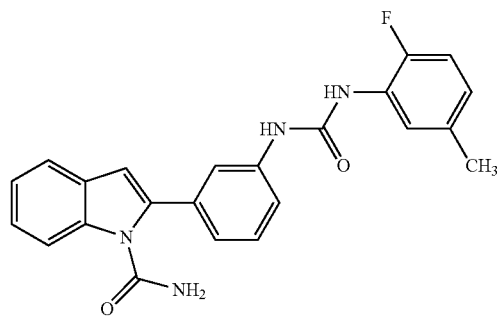 [SMILES: Cc1ccc(F)c(NC(=O)Nc2cccc(-c3cc4ccccc4n3C(N)=O)c2)c1]

2-[3-({[(2-fluoro-5-methylphenyl)amino]carbonyl}amino)phenyl]-1H-indole-1-carboxamide $^1$H NMR (DMSO-d$_6$) δ: 9.18 (s, 1H), 8.51 (d, J=2.1 Hz, 1H), 8.01 (dd, J=7.9, 1.5 Hz, 1H), 7.90 (br. s., 1H), 7.82 (br. s., 1H), 7.72 (d, J=8.2 Hz, 1H), 7.65 (t, J=1.6 Hz, 1H), 7.62 (d, J=7.9 Hz, 1H), 7.46 (dd, J=8.2, 0.9 Hz, 1H), 7.37 (t, J=7.8 Hz, 1H), 7.24-7.28 (m, 1H), 7.15-7.19 (m, 2H), 7.11 (dd, J=11.3, 8.4 Hz, 1H), 6.79-6.82 (m, 1H), 6.77 (s, 1H), 2.27 (s, 3H).

Indole Carbamate with Thiophene

Example 25

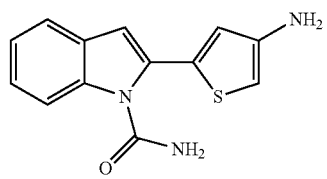 [SMILES: NC(=O)n1c(-c2cc(N)cs2)cc2ccccc21]

2-(4-amino-2-thienyl)-1H-indole-1-carboxamide

To the solution of iodoaniline (4.38 g, 20 mmol, 1 eq) in HOAc—H$_2$O (2:1, 48 mL) was added a solution of potassium cyanate (3.38 g, 2 eq) in H$_2$O (80 mL) at room temperature. The reaction mixture was stirred at room temp for 15 minutes then the white precipitates were filtered using a Buchner funnel and washed with water. The white solid was isolated, treated with ethanol, and stirred at room temp for 24 hours. 1-(2-iodophenyl)urea was obtained as white solid upon filtration in amount of 4.552 g.

$^1$H NMR (DMSO-d$_6$) δ: 7.79 (ddd, J=16.9, 8.0, 1.5 Hz, 2H), 7.58 (s, 1H), 7.26-7.30 (m, 1H), 6.76 (td, J=7.6, 1.5 Hz, 1H), 6.33 (br. s., 2H).

To a degassed solution of 1-(2-iodophenyl)urea (2.62 g, 10 mmol, 1 eq), ethynyltrimethyl silane (4.16 mL, 3 eq), and triethylamine (5.58 mL, 4 eq) in anhydrous DMF (15 mL) was added bis(triphenylphosphine)palladium(II) dichloride (702 mg, 0.1 eq) and copper(I) iodide (190.4 mg, 0.1 eq). After the reaction mixture was stirred at room temperature for 30 minutes, it was partitioned between aqueous ammonium chloride and ethyl acetate. The organic layer was isolated, washed further with saturated sodium bicarbonate, brine, and lastly dried with sodium sulfate. The upper solution was decanted, concentrated, and the brown solid residue was treated with a small amount of DCM. The mixture was stirred at room temperature for 30 minute and filtered to obtain 1-{2-[(trimethylsilyl)ethynyl]phenyl}urea as a white solid in 1.645 g. The filtrate was concentrated and the residue was subject to a gradient column chromatography (EtOAc-hex from 1:100 to 1:1) to render 1-{2-[(trimethylsilyl)ethynyl]phenyl}urea with a second crop of 0.432 g in a total yield of 90%.

$^1$H NMR (DMSO-$d_6$) δ: 7.98 (d, J=7.9 Hz, 1H), 7.65 (s, 1H), 7.35 (dd, J=7.6, 1.5 Hz, 1H), 7.26-7.30 (m, 1H), 6.92 (td, J=7.6, 1.0 Hz, 1H), 6.42 (br. s., 2H), 0.27 (s, 9H).

To the brown solution of 1-{2-[(trimethylsilyl)ethynyl]phenyl}urea (2 g, 8.6 mmol, 1 eq) in THF-MeOH (1:1, 100 mL) at 0° C. was added potassium carbonate (3.574 g, 3 eq) and the reaction mixture was stirred at 0° C. for 45 minutes. The mixture was then filtered through a sinter funnel and the brown filtrate was concentrated under reduced pressure to a lesser amount which was partitioned between aqueous ammonium chloride and ethyl acetate.

The organic layer was isolated, washed with brine, dried with anhydrous sodium sulfate.

The upper solution was decanted, concentrated, and the redish solid residue was treated with a small amount of DCM followed by a small amount of EtOAc-Hex (1:9). After the mixture was stirred at room temp for 30 minutes, it was filtered and a redish brown solid was obtained. The solid was further subject to a column chromatography [from DCM to MeOH-DCM (1:25)]. The product fractions were collected, concentrated, and the solid residue was triturated with EtOAc-Hex (1:15) to yield 1-(2-ethynylphenyl)urea as white solid upon filtration in amount of 1.07 g.

$^1$H NMR (DMSO-$d_6$) δ: 8.10 (d, J=8.2 Hz, 1H), 7.89 (s, 1H), 7.37 (dd, J=7.9, 1.5 Hz, 1H), 7.26-7.30 (m, 1H), 6.91 (td, J=7.5, 1.2 Hz, 1H), 6.44 (br. s., 2H), 4.55 (s, 1H)

To a degassed solution of 2-bromo-4-(N-tert-butyloxycarbonylamino)thiophene (261 mg, 0.94 mmol, 1 eq), 1-(2-ethynylphenyl)urea (200 mg, 1.5 eq), and triphenylphosphine (6.2 mg, 0.025 eq) in anhydrous triethylamine (2 mL) and DMF (0.5 mL) was added bis(triphenylphosphine)palladium(II) dichloride (66 mg, 0.1 eq) and copper(I) iodide (18 mg, 0.1 eq). The mixture was stirred and heated at 80° C. for 30 minutes, then cooled to room temperature and diluted with ethyl acetate. It was washed sequentially with aqueous ammonium chloride, saturated aqueous sodium bicarbonate, brine, and lastly dried with anhydrous sodium sulfate. The upper solution was decanted, concentrated, and the solid residue was subject to a gradient column chromatography (EtOAc-Hex from 1;100 to 1:1) to yield tert-butyl[5-({2-[(aminocarbonyl)amino]phenyl}ethynyl)-3-thienyl]carbamate as a yellow oil (194 mg) which was converted to a foam after dried in vacuo.

$^1$H NMR (DMSO-$d_6$) δ: 9.77 (br. s., 1H), 8.07 (d, J=7.9 Hz, 1H), 7.99 (s, 1H), 7.44 (dd, J=7.9, 1.5 Hz, 1H), 7.26-7.34 (m, 3H), 6.96 (td, J=7.6, 1.0 Hz, 1H), 6.42 (br. s., 2H), 1.47 (s, 9H).

To a degassed solution of tert-butyl[5-({2-[(aminocarbonyl)amino]phenyl}ethynyl)-3-thienyl]carbamate (112 mg, 0.314 mmol, 1 eq) in anhydrous acetonitrile (2 mL) was added bis(acetonitrile)dichloropalladium(II) (16.3 mg, 0.2 eq). After the reaction mixture was heated at 90° C. for 50 minutes, it was cooled to room temp, and diluted with ethyl acetate. The mixture was washed with aqueous ammonium chloride, water, and brine, and lastly dried with anhydrous sodium sulfate. The upper solution was decanted, concentrated, and the dark brown mixture was subject to a gradient column chromatography (EtOAc-hex from 1; 100 to 1:5) to yield tert-butyl {5-[1-(aminocarbonyl)-1H-indol-2-yl]-3-thienyl}carbamate as white powder in amount of 23 mg.

$^1$H NMR (DMSO-$d_6$) δ: 9.73 (br. s., 1H), 8.00 (br. s., 2H), 7.63 (d, J=8.5 Hz, 1H), 7.58 (d, J=7.6 Hz, 1H), 7.25 (ddd, J=8.2, 7.2, 1.0 Hz, 1H), 7.21 (s, 2H), 7.16 (t, J=7.5 Hz, 1H), 6.75 (s, 1H), 1.48 (s, 9H).

To the mixture of tert-butyl {5-[1-(aminocarbonyl)-1H-indol-2-yl]-3-thienyl}carbamate (20 mg, 0.056 mmol, 1 eq) in anhydrous DCM (1 mL) at 0° C. was added dropwise trifluoroacetic acid (0.2 mL) and the resulting reaction solution was stirred at 0° C. for 45 minutes. An additional trifluoroacetic acid (0.2 mL) was added followed by a stirring at room temperature for 15 minutes. The solution was partitioned between saturated aqueous sodium bicarbonate and ethyl acetate. The organic layer was isolated, washed once with brine, and dried with anhydrous sodium sulfate. The Upper solution was decanted, concentrated, and the brown oily residue was subject to a column chromatography (EtOAc-Hex 1:10 to 3:1) to yield 2-(4-amino-2-thienyl)-1H-indole-1-carboxamide as a yellow oil in amount of 11 mg.

$^1$H NMR (DMSO-$d_6$) δ: 7.94-8.01 (m, 2H), 7.60 (d, J=8.2 Hz, 1H), 7.56 (d, J=7.6 Hz, 1H), 7.21-7.24 (m, 1H), 7.13 (t, J=7.5 Hz, 1H), 6.77 (d, J=1.5 Hz, 1H), 6.68 (s, 1H), 6.02 (d, J=1.5 Hz, 1H), 4.92 (br. s., 2H).

Example 26

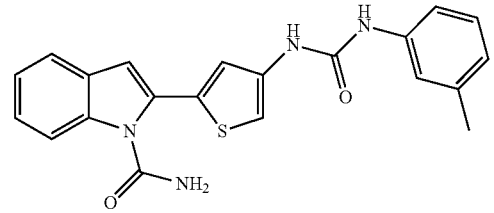 [SMILES: Cc1cccc(NC(=O)Nc2csc(-c3cc4ccccc4n3C(N)=O)c2)c1]

2-[4-({[(3-methylphenyl)amino]carbonyl}amino)-2-thienyl]-1H-indole-1-carboxamide To the solution of 2-(4-amino-2-thienyl)-1H-indole-1-carboxamide (51.4 mg, 0.2 mmol, 1 eq) in anhydrous THF (2 mL) was added m-tolyl isocyanate (25 µL, 1 eq) and the reaction solution was stirred at room temperature for one hour. It was then diluted with ethyl acetate, washed with aqueous ammonium chloride, saturated aqueous sodium bicarbonate, brine, and lastly dried with anhydrous sodium sulfate. The upper solution was decanted, concentrated and the solid residue was treated with a small amount of dichloromethane and EtOAc-Hex (1:4). The mixture was stirred at room temperature for one hour followed by a filtration to give 2-[4-({[(3-methylphenyl)amino]carbonyl}amino)-2-thienyl]-1H-indole-1-carboxamide as a slightly brown solid in amount of 73 mg.

$^1$H NMR (DMSO-$d_6$) δ: 9.03 (s, 1H), 8.50 (s, 1H), 8.06 (s, 2H), 7.63 (d, J=8.5 Hz, 1H), 7.59 (d, J=7.9 Hz, 1H), 7.30-7.32 (m, 2H), 7.26 (ddd, J=8.2, 7.2, 1.0 Hz, 1H), 7.22-7.24 (m, 2H), 7.14-7.18 (m, 2H), 6.80 (s, 1H), 6.79 (d, J=7.6 Hz, 1H), 2.28 (s, 3H).

The following Examples were synthesized according to the procedure described in Example 26.

Example 27

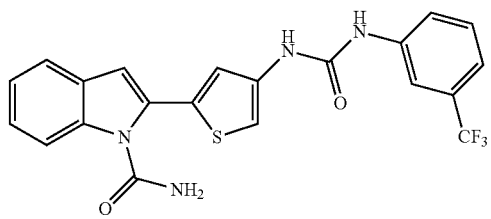 [SMILES: NC(=O)n1c(-c2cc(NC(=O)Nc3cccc(C(F)(F)F)c3)cs2)cc2ccccc21]

2-{4-[({[3-(trifluoromethyl)phenyl]amino}carbonyl)amino]-2-thienyl}-1H-indole-1-carboxamide $^1$H NMR (DMSO-d$_6$) δ: 9.21 (s, 1H), 8.98 (s, 1H), 8.06 (s, 2H), 8.03 (s, 1H), 7.64 (d, J=8.5 Hz, 1H), 7.58-7.61 (m, 2H), 7.51 (t, J=7.9 Hz, 1H), 7.35 (d, J=1.5 Hz, 1H), 7.31 (d, J=7.6 Hz, 1H), 7.25-7.28 (m, 2H), 7.15-7.18 (m, 1H), 6.81 (s, 1H).

Example 28

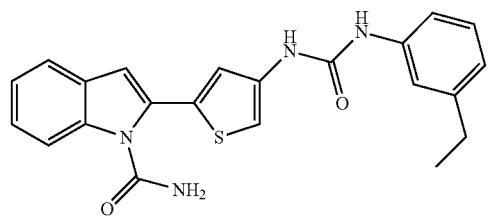 [SMILES: CCc1cccc(NC(=O)Nc2csc(-c3cc4ccccc4n3C(N)=O)c2)c1]

2-[4-({[(3-ethylphenyl)amino]carbonyl}amino)-2-thienyl]-1H-indole-1-carboxamide $^1$H NMR (DMSO-d$_6$) δ: 9.03 (s, 1H), 8.52 (s, 1H), 8.06 (s, 2H), 7.63 (dd, J=8.2, 0.6 Hz, 1H), 7.59 (d, J=7.6 Hz, 1H), 7.33 (s, 1H), 7.31 (d, J=1.5 Hz, 1H), 7.24-7.28 (m, 2H), 7.24 (d, J=1.5 Hz, 1H), 7.15-7.20 (m, 2H), 6.82 (d, J=7.3 Hz, 1H), 6.81 (s, 1H), 2.58 (q, J=7.6 Hz, 2H), 1.18 (t, J=7.6 Hz, 3H).

Example 29

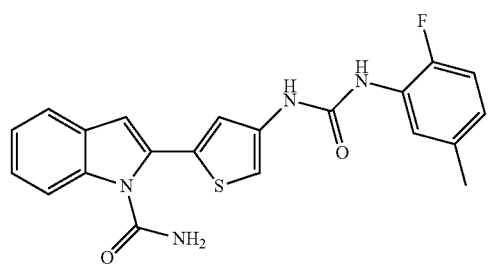 [SMILES: Cc1ccc(F)c(NC(=O)Nc2csc(-c3cc4ccccc4n3C(N)=O)c2)c1]

2-[4-({[(2-fluoro-5-methylphenyl)amino]carbonyl}amino)-2-thienyl]-1H-indole-1-carboxamide $^1$H NMR (DMSO-d$_6$) δ: 9.42 (s, 1H), 8.38 (d, J=2.3 Hz, 1H), 8.07 (s, 2H), 7.99 (dd, J=7.6, 1.8 Hz, 1H), 7.63 (d, J=8.2 Hz, 1H), 7.60 (d, J=7.6 Hz, 1H), 7.33 (d, J=1.5 Hz, 1H), 7.26 (ddd, J=8.2, 7.0, 1.2 Hz, 1H), 7.21 (d, J=1.5 Hz, 1H), 7.15-7.18 (m, 1H), 7.10 (dd, J=11.3, 8.4 Hz, 1H), 6.82 (s, 1H), 6.80 (ddd, J=7.8, 5.2, 2.2 Hz, 1H), 2.28 (s, 3H).

Example 30

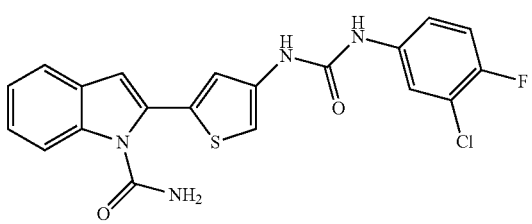 [SMILES: NC(=O)n1c(-c2cc(NC(=O)Nc3ccc(F)c(Cl)c3)cs2)cc2ccccc21]

2-[4-({[(3-chloro-4-fluorophenyl)amino]carbonyl}amino)-2-thienyl]-1H-indole-1-carboxamide $^1$H NMR (DMSO-d$_6$) δ: 9.18 (s, 1H), 8.81 (s, 1H), 8.06 (s, 2H), 7.80-7.83 (m, 1H), 7.63 (d, J=8.2 Hz, 1H), 7.59 (d, J=7.6 Hz, 1H), 7.31-7.36 (m, 3H), 7.24-7.28 (m, 2H), 7.15-7.18 (m, 1H), 6.80 (s, 1H).

Example 31

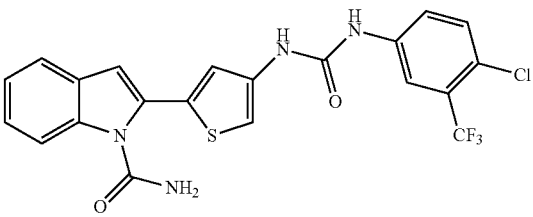 [SMILES: NC(=O)n1c(-c2cc(NC(=O)Nc3ccc(Cl)c(C(F)(F)F)c3)cs2)cc2ccccc21]

2-{4-[({[4-chloro-3-(trifluoromethyl)phenyl]amino}carbonyl)amino]-2-thienyl}-1H-indole-1-carboxamide $^1$H NMR (DMSO-d$_6$) δ: 9.28 (s, 1H), 9.11 (s, 1H), 8.12 (d, J=2.3 Hz, 1H), 8.06 (s, 2H), 7.66-7.69 (m, 1H), 7.61 (td, J=12.0, 8.2 Hz, 3H), 7.36 (d, J=1.5 Hz, 1H), 7.28 (d, J=1.5 Hz, 1H), 7.24-7.27 (m, 1H), 7.15-7.18 (m, 1H), 6.81 (s, 1H).

Example 32

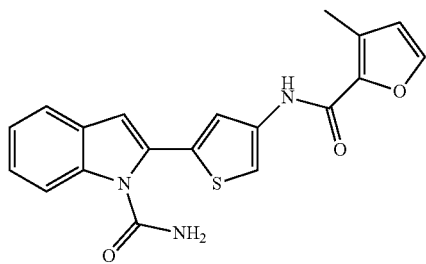 [SMILES: Cc1ccoc1C(=O)Nc1csc(-c2cc3ccccc3n2C(N)=O)c1]

2-{4-[(3-methyl-2-furoyl)amino]-2-thienyl}-1H-indole-1-carboxamide

To the solution of 2-(4-amino-2-thienyl)-1H-indole-1-carboxamide (51.4 mg, 0.2 mmol, 1 eq) and 3-methyl-furan-2-carboxylic acid (25.2 mg, 1 eq) in anhydrous DCE (2 mL) was added 4-(dimethylamino)pyridine (4.9 mg, 0.2 eq) and N-(3-dimethylaminopropyl)-N'-ethylcarbodiimide hydrochloride (46.1 mg, 1.2 eq). After the reaction was stirred at 60° C. for 1 hour, it was diluted with ethyl acetate, washed sequentially with aqueous ammonium chloride, saturated aqueous sodium bicarbonate, brine, and lastly dried with anhydrous sodium sulfate. The upper clear solution was decanted, concentrated, and the oily residue was subject to a gradient column chromatography (EtOAc-Hex 1:100 to 1:2) to yield 2-{4-[(3-methyl-2-furoyl)amino]-2-thienyl}-1H-indole-1-carboxamide as a yellow solid in amount of 42 mg.

$^1$H NMR (DMSO-d$_6$) δ: 10.66 (s, 1H), 8.04 (br. s., 2H), 7.79 (d, J=1.8 Hz, 1H), 7.72 (d, J=1.5 Hz, 1H), 7.64 (d, J=8.5 Hz, 1H), 7.60 (d, J=7.9 Hz, 1H), 7.58 (d, J=1.5 Hz, 1H), 7.26 (ddd, J=8.2, 7.2, 1.0 Hz, 1H), 7.15-7.18 (m, 1H), 6.79 (s, 1H), 6.59 (d, J=1.5 Hz, 1H), 2.36 (s, 3H).

Example 33 was synthesized following the procedure described in Example 32.

Example 33

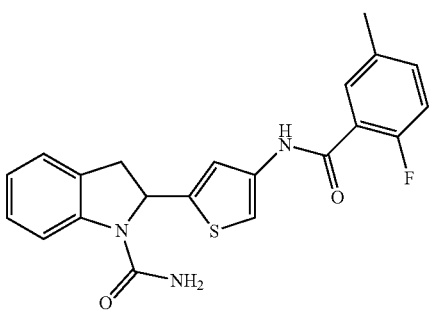 [SMILES: Cc1ccc(F)c(C(=O)Nc2csc(C3Cc4ccccc4N3C(N)=O)c2)c1]

2-{4-[(2-fluoro-5-methylbenzoyl)amino]-2-thienyl}-1H-indole-1-carboxamide $^1$H NMR (DMSO-d$_6$) δ: 10.85 (s, 1H), 8.06 (br. s., 2H), 7.73 (d, J=1.5 Hz, 1H), 7.64 (dd, J=8.2, 0.6 Hz, 1H), 7.60 (d, J=7.6 Hz, 1H), 7.48 (dd, J=6.6, 1.9 Hz, 1H), 7.40 (d, J=1.5 Hz, 1H), 7.36-7.39 (m, 1H), 7.27 (ddd, J=8.2, 7.2, 1.0 Hz, 1H), 7.23 (dd, J=10.1, 8.7 Hz, 1H), 7.15-7.18 (m, 1H), 6.81 (s, 1H), 2.35 (s, 3H).

Biological data for the compounds of the present invention was generated by use of the following assays.

VEGFR2 Kinase Assay

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N H$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight @37° C./5% CO2. Cells were loaded with calcium indicator Fluo-4 for 45 minutes at 37° C. Cells were washed 2 times (EIx405, Biotek Instruments) to remove extracellular dye. For screening, cells were pre-incubated with test agents for 30 minutes, at a single concentration (10 uM) or at concentrations ranging from 0.0001 to 10.0 uM followed by VEGF$_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. IC$_{50}$ values for test compounds were calculated from % inhibition of VEGF stimulated responses in the absence of inhibitor.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Cellular Assay

Automated FLIPR (Fluorometric Imaging Plate Reader) technology was used to screen for inhibitors of PDGF-induced increases in intracellular calcium levels in fluorescent dye loaded endothelial cells. NHDF-Ad (Normal Human Dermal Fibroblasts, Adult; Lonza) were seeded in 384-well fibronectin coated black-walled plates overnight @37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by PDGF-BB stimulation (30 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF-BB stimulated responses in the absence of inhibitor.

The biological results for the various compounds are shown in Tables 2, 3, 4 and 5 below.

TABLE 2

In vitro VEGFR2 and PDGFRβ data

| Ex. | Structure | Enzyme VEGFR2 $IC_{50}$ (nM) | Receptor VEGFR2 $IC_{50}$ (nM) | Enzyme PDGFβ $IC_{50}$ (nM) |
|---|---|---|---|---|
| 1 | ![structure] | 3 | 13 | 10 |
| 2 | ![structure] | 5 | 11 | 10 |
| 3 | ![structure] | 6 | 17 | 14 |

TABLE 2-continued

In vitro VEGFR2 and PDGFRβ data

| Ex. | Structure | Enzyme VEGFR2 IC$_{50}$ (nM) | Receptor VEGFR2 IC$_{50}$ (nM) | Enzyme PDGFβ IC$_{50}$ (nM) |
|---|---|---|---|---|
| 4 | indole-1-carboxamide-2-(4-(3-(3-isopropylphenyl)ureido)phenyl) | 6 | 15 | 16 |
| 5 | indole-1-carboxamide-2-(4-(3-(3-chloro-4-fluorophenyl)ureido)phenyl) | 8 | 97 | 19 |
| 6 | indole-1-carboxamide-2-(4-(3-(3-(trifluoromethyl)phenyl)ureido)phenyl) | 9 | 58 | 28 |
| 7 | indole-1-carboxamide-2-(4-(3-(2-fluoro-5-methylphenyl)ureido)phenyl) | 9 | 41 | 20 |
| 8 | indole-1-carboxamide-2-(4-(3-(3-methoxyphenyl)ureido)phenyl) | 11 | 45 | 12 |

TABLE 2-continued
In vitro VEGFR2 and PDGFRβ data
| Ex. | Structure | Enzyme VEGFR2 IC$_{50}$ (nM) | Receptor VEGFR2 IC$_{50}$ (nM) | Enzyme PDGFβ IC$_{50}$ (nM) |
|---|---|---|---|---|
| 9 | 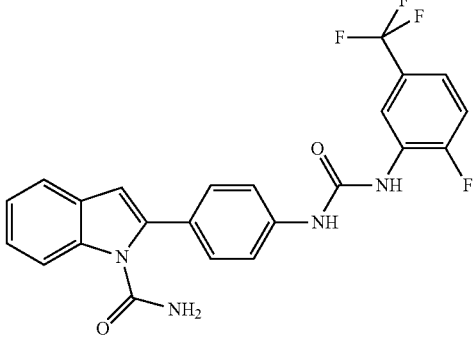 | 11 | 139 | 55 |
| 10 | 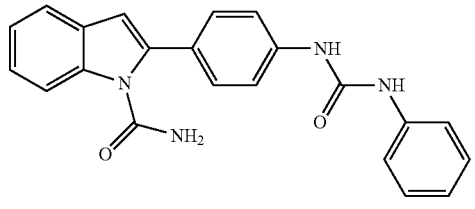 [SMILES: NC(=O)n1c(-c2ccc(NC(=O)Nc3ccccc3)cc2)cc2ccccc21] | 22 | 150 | 23 |
| 11 | 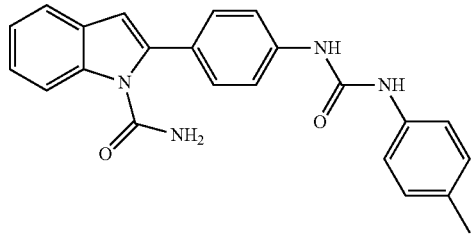 [SMILES: Cc1ccc(NC(=O)Nc2ccc(-c3cc4ccccc4n3C(N)=O)cc2)cc1] | 23 | >10,000 | 11 |
| 12 | 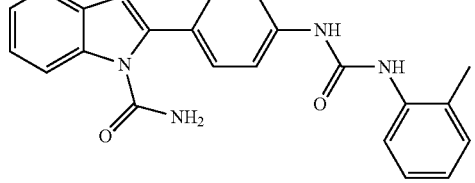 | 174 | NA | 118 |

TABLE 3

In vitro VEGFR2 and PDGFRβ data

| Ex. | Structure | Enzyme VEGFR2 IC$_{50}$ (nM) | Receptor VEGFR2 IC$_{50}$ (nM) | Enzyme PDGFβ IC$_{50}$ (nM) |
|---|---|---|---|---|
| 19 | 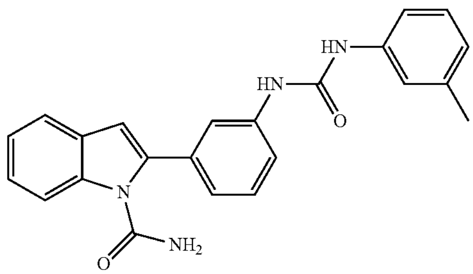 [SMILES: Cc1cccc(NC(=O)Nc2cccc(-c3cc4ccccc4n3C(N)=O)c2)c1] | 276 | NA | NA |
| 20 | 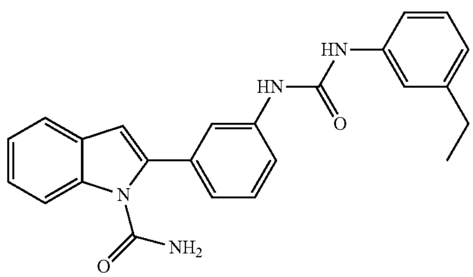 [SMILES: CCc1cccc(NC(=O)Nc2cccc(-c3cc4ccccc4n3C(N)=O)c2)c1] | 240 | NA | NA |
| 21 | 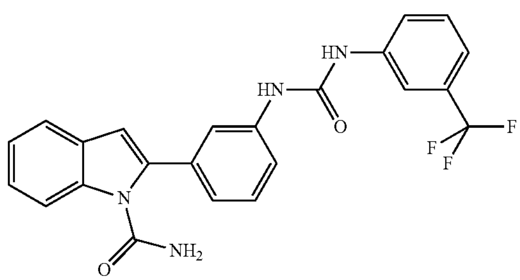 [SMILES: NC(=O)n1c(-c2cccc(NC(=O)Nc3cccc(C(F)(F)F)c3)c2)cc2ccccc21] | 254 | NA | 3310 |
| 22 | 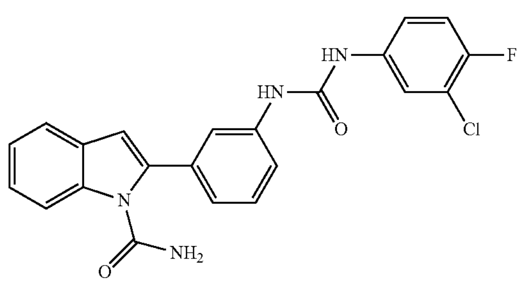 [SMILES: NC(=O)n1c(-c2cccc(NC(=O)Nc3ccc(F)c(Cl)c3)c2)cc2ccccc21] | 249 | NA | >10,000 |
| 23 | 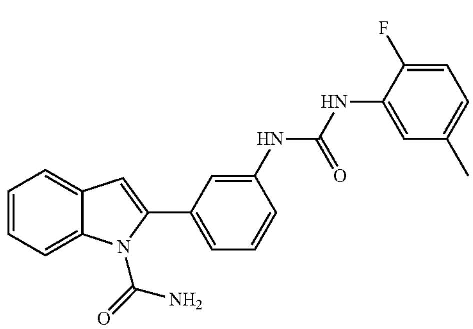 [SMILES: Cc1ccc(F)c(NC(=O)Nc2cccc(-c3cc4ccccc4n3C(N)=O)c2)c1] | 334 | NA | 3030 |

TABLE 3-continued

In vitro VEGFR2 and PDGFRβ data

| Ex. | Structure | Enzyme VEGFR2 IC$_{50}$ (nM) | Receptor VEGFR2 IC$_{50}$ (nM) | Enzyme PDGFβ IC$_{50}$ (nM) |
| --- | --- | --- | --- | --- |
| 24 | 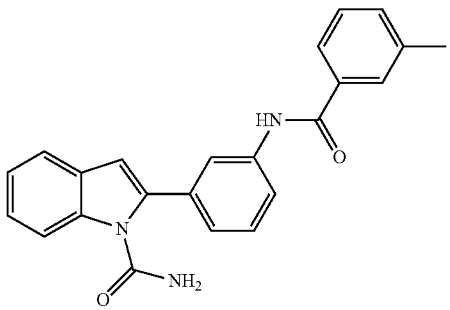 [SMILES: Cc1cccc(C(=O)Nc2cccc(-c3cc4ccccc4n3C(N)=O)c2)c1] | 1174 | NA | NA |

TABLE 4

In vitro VEGFR2 and PDGFRβ data

| Ex. | Structure | Enzyme VEGFR2 IC$_{50}$ (nM) | Receptor VEGFR2 IC$_{50}$ (nM) | Enzyme PDGFβ IC$_{50}$ (nM) |
| --- | --- | --- | --- | --- |
| 26 | 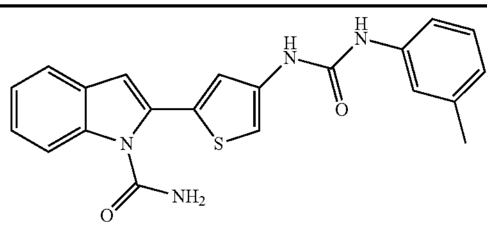 | 67 | 508 | 1141 |
| 27 | 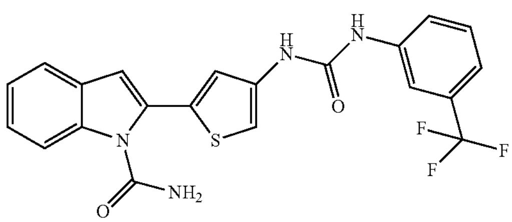 [SMILES: NC(=O)n1c(-c2cc(NC(=O)Nc3cccc(C(F)(F)F)c3)cs2)cc2ccccc21] | 93 | 1209 | 152 |
| 28 | 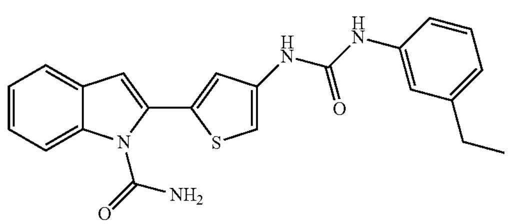 [SMILES: CCc1cccc(NC(=O)Nc2csc(-c3cc4ccccc4n3C(N)=O)c2)c1] | 60 | NA | 264 |
| 29 | 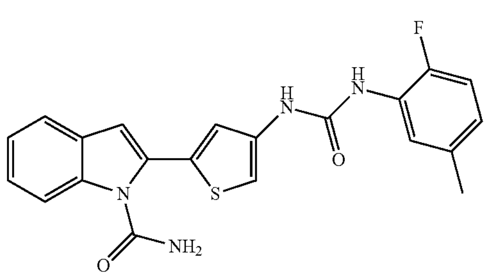 [SMILES: Cc1ccc(F)c(NC(=O)Nc2csc(-c3cc4ccccc4n3C(N)=O)c2)c1] | 94 | NA | 4608 |

TABLE 4-continued
In vitro VEGFR2 and PDGFRβ data
| Ex. | Structure | Enzyme VEGFR2 IC$_{50}$ (nM) | Receptor VEGFR2 IC$_{50}$ (nM) | Enzyme PDGFβ IC$_{50}$ (nM) |
|---|---|---|---|---|
| 30 | 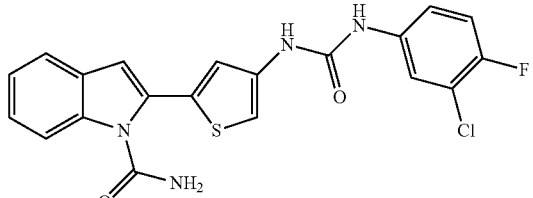 | 83 | NA | >10,000 |
| 31 | 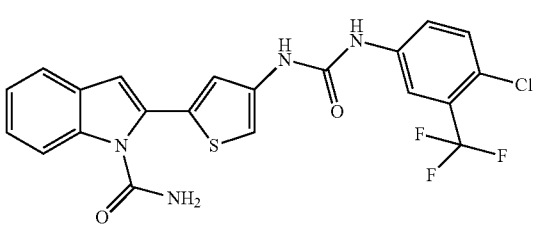 [SMILES: NC(=O)n1c(-c2cc(NC(=O)Nc3ccc(Cl)c(C(F)(F)F)c3)cs2)cc2ccccc21] | 131 | 7350 | 151 |
TABLE 5
In vitro VEGFR2 and PDGFRβ data
| Ex. | Structure | Enzyme VEGFR2 IC$_{50}$ (nM) | Receptor VEGFR2 IC$_{50}$ (nM) | Enzyme PDGFβ IC$_{50}$ (nM) |
|---|---|---|---|---|
| 32 | 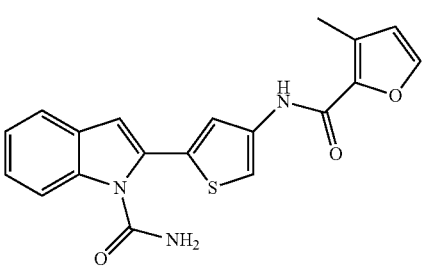 [SMILES: Cc1ccoc1C(=O)Nc1csc(-c2cc3ccccc3n2C(N)=O)c1] | 3185 | NA | >10,000 |
| 33 | 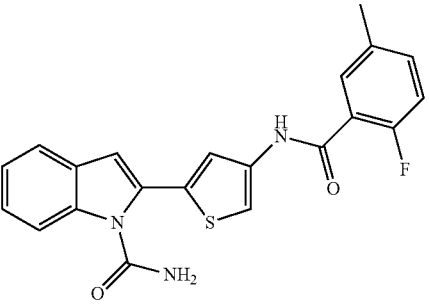 [SMILES: Cc1ccc(F)c(C(=O)Nc2csc(-c3cc4ccccc4n3C(N)=O)c2)c1] | 3647 | NA | >10,000 |

What is claimed is:

1. A compound represented by Formula I or an enatiomer, diastereoisomer or pharmaceutically acceptable salt thereof:

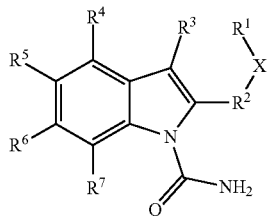

Formula I wherein:

$R^1$ is substituted or unsubstituted heterocycle or substituted or unsubstituted aryl;

X is

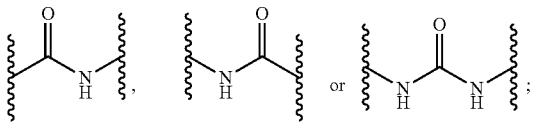 [SMILES: *NC(*)=O ; *NC(*)=O ; *NC(=O)N*]

$R^2$ is substituted or unsubstituted heterocycle or substituted or unsubstituted aryl;

$R^3$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{121})_2$ or $(CR^8R^9)_aN(R^{11}R^{12})_2$;

$R^4$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{12})_2$, $(CR^8R^9)_aN(R^{11})C(O)OR^{10}$, $(CR^8R^9)_aN(R^{11})C(O)N(R^{11}R^{121})_2$ or $(CR^8R^9)_aN(R^{11}R^{12})_2$;

$R^5$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{121})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^6$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{121})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^7$ is hydrogen, substituted or unsubstituted $C_1$-$C_8$ alkyl, substituted or unsubstituted heterocycle, substituted or unsubstituted aryl, halogen, hydrogen, $(CR^8R^9)_aC(O)OR^{10}$, $(CR^8R^9)_aOR^{10}$, $(CR^8R^9)_aN(R^{11})C(O)OR^{10}$, $(CR^8R^9)_aC(O)N(R^{11}R^{121})_2$, $(CR^8R^9)_aN(R^{11})C(O)OR^{10}$, $(CR^8R^9)_aN(R^{11})C(O)N(R^{11}R^{12})_2$ or $(CR^8R^9)_aN(R^{11}R^{12})_2$;

$R^8$ is substituted or unsubstituted $C_{1-8}$ alkyl, hydrogen, fluoro, —$CH_2OH$, —$OH$, $COCH_3$, $CH_2CH_2OH$, $CH_2CH_2CH_2OH$ or $CH_2CH_2OCH_2CH_2OH$;

$R^9$ is substituted or unsubstituted $C_{1-8}$ alkyl, hydrogen, fluoro or —$OH$;

$R^{10}$ is substituted or unsubstituted $C_{1-8}$ alkyl or hydrogen;

$R^{11}$ is substituted or unsubstituted $C_{1-8}$ alkyl, hydrogen or can form together with the N and $R^{12}$ a substituted or unsubstituted heterocycle;

$R^{12}$ is substituted or unsubstituted $C_{1-8}$ alkyl, hydrogen or can form together with the N and $R^{11}$ a substituted or unsubstituted heterocycle; and a is 0, 1, 2, 3 or 4.

2. The compound according to claim 1, wherein:

X is

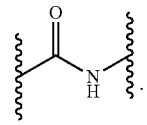

3. The compound according to claim 1, wherein:

X is

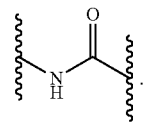

4. The compound according to claim 1, wherein:

X is

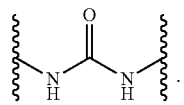

5. The compound according to claim 1, wherein:

$R^1$ is substituted or unsubstituted heterocycle;

X is

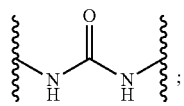 [SMILES: *NC(=O)N*]

$R^2$ is substituted or unsubstituted aryl;

$R^3$ is hydrogen, substituted or unsubstituted $C_1$-$C_8$ alkyl, halogen;

$R^4$ is hydrogen, substituted or unsubstituted $C_1$-$C_8$ alkyl, halogen;

$R^5$ is hydrogen, substituted or unsubstituted $C_1$-$C_8$ alkyl, halogen;

$R^6$ is hydrogen, substituted or unsubstituted $C_1$-$C_8$ alkyl, halogen; and $R^7$ is hydrogen, substituted or unsubstituted $C_1$-$C_8$ alkyl, halogen.

6. The compound according to claim 1, wherein:
R$^1$ is substituted or unsubstituted aryl;
X is

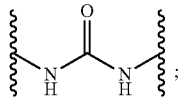

R$^2$ is substituted or unsubstituted heterocycle;
R$^3$ is hydrogen, substituted or unsubstituted C$_1$-C$_8$ alkyl, halogen;
R$^4$ is hydrogen, substituted or unsubstituted C$_1$-C$_8$ alkyl, halogen;
R$^5$ is hydrogen, substituted or unsubstituted C$_1$-C$_8$ alkyl, halogen;
R$^6$ is hydrogen, substituted or unsubstituted C$_1$-C$_8$ alkyl, halogen; and
R$^7$ is hydrogen, substituted or unsubstituted C$_1$-C$_8$ alkyl, halogen.

7. The compound according to claim 1, wherein
R$^1$ is substituted or unsubstituted aryl;
X is

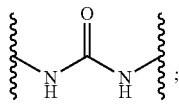

R$^2$ is substituted or unsubstituted aryl;
R$^3$ is hydrogen, substituted or unsubstituted C$_1$-C$_8$ alkyl, halogen;
R$^4$ is hydrogen, substituted or unsubstituted C$_1$-C$_8$ alkyl, halogen;
R$^5$ is hydrogen, substituted or unsubstituted C$_1$-C$_8$ alkyl, halogen;
R$^6$ is hydrogen, substituted or unsubstituted C$_1$-C$_8$ alkyl, halogen; and
R$^7$ is hydrogen, substituted or unsubstituted C$_1$-C$_8$ alkyl, halogen.

8. The compound according to claim 1, wherein
R$^1$ is substituted or unsubstituted heterocycle;
X is

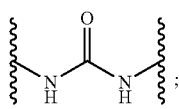

R$^2$ is substituted or unsubstituted heterocyle;
R$^3$ is hydrogen, substituted or unsubstituted C$_1$-C$_8$ alkyl, halogen;
R$^4$ is hydrogen, substituted or unsubstituted C$_1$-C$_8$ alkyl, halogen;
R$^5$ is hydrogen, substituted or unsubstituted C$_1$-C$_8$ alkyl, halogen;
R$^6$ is hydrogen, substituted or unsubstituted C$_1$-C$_8$ alkyl, halogen; and
R$^7$ is hydrogen, substituted or unsubstituted C$_1$-C$_8$ alkyl, halogen.

9. The compound according to claim 1, wherein
R$^1$ is substituted or unsubstituted heterocycle;
X is

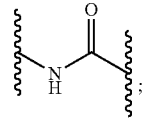 [SMILES: *NC(*)=O]

R$^2$ is substituted or unsubstituted aryl;
R$^3$ is hydrogen, substituted or unsubstituted C$_1$-C$_8$ alkyl, halogen;
R$^4$ is hydrogen, substituted or unsubstituted C$_1$-C$_8$ alkyl, halogen;
R$^5$ is hydrogen, substituted or unsubstituted C$_1$-C$_8$ alkyl, halogen;
R$^6$ is hydrogen, substituted or unsubstituted C$_1$-C$_8$ alkyl, halogen; and
R$^7$ is hydrogen, substituted or unsubstituted C$_1$-C$_8$ alkyl, halogen.

10. The compound according to claim 1, wherein
R$^1$ is substituted or unsubstituted aryl;
X is

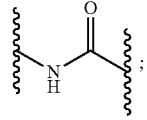 [SMILES: *NC(*)=O]

R$^2$ is substituted or unsubstituted heterocycle;
R$^3$ is hydrogen, substituted or unsubstituted C$_1$-C$_8$ alkyl, halogen;
R$^4$ is hydrogen, substituted or unsubstituted C$_1$-C$_8$ alkyl, halogen;
R$^5$ is hydrogen, substituted or unsubstituted C$_1$-C$_8$ alkyl, halogen;
R$^6$ is hydrogen, substituted or unsubstituted C$_1$-C$_8$ alkyl, halogen; and
R$^7$ is hydrogen, substituted or unsubstituted C$_1$-C$_8$ alkyl, halogen.

11. The compound according to claim 1, wherein
R$^1$ is substituted or unsubstituted aryl;
X is

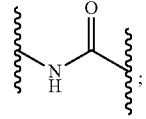 [SMILES: *NC(*)=O]

R$^2$ is substituted or unsubstituted aryl;
R$^3$ is hydrogen, substituted or unsubstituted C$_1$-C$_8$ alkyl, halogen;
R$^4$ is hydrogen, substituted or unsubstituted C$_1$-C$_8$ alkyl, halogen;
R$^5$ is hydrogen, substituted or unsubstituted C$_1$-C$_8$ alkyl, halogen;
R$^6$ is hydrogen, substituted or unsubstituted C$_1$-C$_8$ alkyl, halogen; and
R$^7$ is hydrogen, substituted or unsubstituted C$_1$-C$_8$ alkyl, halogen.

12. The compound according to claim 1, wherein R¹ is substituted or unsubstituted heterocycle; X is

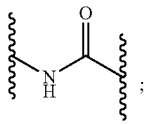

R² is substituted or unsubstituted heterocycle;
R³ is hydrogen, substituted or unsubstituted $C_1$-$C_8$ alkyl, halogen;
R⁴ is hydrogen, substituted or unsubstituted $C_1$-$C_8$ alkyl, halogen;
R⁵ is hydrogen, substituted or unsubstituted $C_1$-$C_8$ alkyl, halogen;
R⁶ is hydrogen, substituted or unsubstituted $C_1$-$C_8$ alkyl, halogen; and
R⁷ is hydrogen, substituted or unsubstituted $C_1$-$C_8$ alkyl, halogen.

13. A compound according to claim 1, selected from:
2-[4-({[(3-ethylphenyl)amino]carbonyl}amino)phenyl]-1H-indole-1-carboxamide;
methyl 1-(aminocarbonyl)-2-[4-({[(3-methylphenyl)amino]carbonyl}amino)phenyl]-1H-indole-6-carboxylate;
2-[4-({[(3-methylphenyl)amino]carbonyl}amino)phenyl]-1H-indole-1-carboxamide;
2-[4-({[(3-isopropylphenyl)amino]carbonyl}amino)phenyl]-1H-indole-1-carboxamide;
2-[4-({[(3-chloro-4-fluorophenyl)amino]carbonyl}amino)phenyl]-1H-indole-1-carboxamide;
2-{4-[({[3-(trifluoromethyl)phenyl]amino}carbonyl)amino]phenyl}-1H-indole-1-carboxamide;
2-[4-({[(2-fluoro-5-methylphenyl)amino]carbonyl}amino)phenyl]-1H-indole-1-carboxamide;
2-[4-({[(3-methoxyphenyl)amino]carbonyl}amino)phenyl]-1H-indole-1-carboxamide;
2-{4-[({[2-fluoro-5-(trifluoromethyl)phenyl]amino}carbonyl)amino]phenyl}-1H-indole-1-carboxamide;
2-{4-[(anilinocarbonyl)amino]phenyl}-1H-indole-1-carboxamide;
2-[4-({[(4-methylphenyl)amino]carbonyl}amino)phenyl]-1H-indole-1-carboxamide;
2-[4-({[(2-methylphenyl)amino]carbonyl}amino)phenyl]-1H-indole-1-carboxamide;
2-{4-[(2-fluoro-5-methylbenzoyl)amino]phenyl}-1H-indole-1-carboxamide;
2-{4-[(3-methylbenzoyl)amino]phenyl}-1H-indole-1-carboxamide;
2-{4-[(3-methoxybenzoyl)amino]phenyl}-1H-indole-1-carboxamide;
2-[4-(benzoylamino)phenyl]-1H-indole-1-carboxamide;
2-{4-[(3-methyl-2-furoyl)amino]phenyl}-1H-indole-1-carboxamide;
2-(4-{[3-(trifluoromethyl)benzoyl]amino}phenyl)-1H-indole-1-carboxamide;
2-[3-({[(3-methylphenyl)amino]carbonyl}amino)phenyl]-1H-indole-1-carboxamide;
2-[3-({[(3-ethylphenyl)amino]carbonyl}amino)phenyl]-1H-indole-1-carboxamide;
2-{3-[({[3-(trifluoromethyl)phenyl]amino}carbonyl)amino]phenyl}-1H-indole-1-carboxamide;
2-[3-({[(3-chloro-4-fluorophenyl)amino]carbonyl}amino)phenyl]-1H-indole-1-carboxamide;
2-[3-({[(2-fluoro-5-methylphenyl)amino]carbonyl}amino)phenyl]-1H-indole-1-carboxamide;
2-{3-[(3-methylbenzoyl)amino]phenyl}-1H-indole-1-carboxamide;
2-[4-({[(3-methylphenyl)amino]carbonyl}amino)-2-thienyl]-1H-indole-1-carboxamide;
2-{4-[({[3-(trifluoromethyl)phenyl]amino}carbonyl)amino]-2-thienyl}-1H-indole-1-carboxamide;
2-[4-({[(3-ethylphenyl)amino]carbonyl}amino)-2-thienyl]-1H-indole-1-carboxamide;
2-[4-({[(2-fluoro-5-methylphenyl)amino]carbonyl}amino)-2-thienyl]-1H-indole-1-carboxamide;
2-[4-({[(3-chloro-4-fluorophenyl)amino]carbonyl}amino)-2-thienyl]-1H-indole-1-carboxamide;
2-{4-[({[4-chloro-3-(trifluoromethyl)phenyl]amino}carbonyl)amino]-2-thienyl}-1H-indole-1-carboxamide;
2-{4-[(3-methyl-2-furoyl)amino]-2-thienyl}-1H-indole-1-carboxamide; and
2-{4-[(2-fluoro-5-methylbenzoyl)amino]-2-thienyl}-1H-indole-1-carboxamide.

14. A pharmaceutical composition comprising as active ingredient a therapeutically effective amount of a compound according to claim 1 and a pharmaceutically acceptable adjuvant, diluent or carrier.

* * * * *